(12) United States Patent
Reuel et al.

(10) Patent No.: US 10,837,045 B2
(45) Date of Patent: Nov. 17, 2020

(54) OPTICAL NANOSENSORS FOR HYDROLYTIC ENZYME CHARACTERIZATION

(71) Applicant: Iowa State University Research Foundation, Inc., Ames, IA (US)

(72) Inventors: Nigel Forest Reuel, Ames, IA (US); Nathaniel Kallmyer, Whitestown, IN (US)

(73) Assignee: Iowa State University Research Foundation, Inc., Ames, IA (US)

( * ) Notice: Subject to any disclaimer, the term of this patent is extended or adjusted under 35 U.S.C. 154(b) by 130 days.

(21) Appl. No.: 16/259,380

(22) Filed: Jan. 28, 2019

(65) Prior Publication Data

US 2019/0233875 A1   Aug. 1, 2019

Related U.S. Application Data

(60) Provisional application No. 62/623,593, filed on Jan. 30, 2018.

(51) Int. Cl.
| | | |
|---|---|---|
| *G01J 3/46* | (2006.01) | |
| *C12Q 1/34* | (2006.01) | |
| *C12N 9/14* | (2006.01) | |
| *C12Q 1/00* | (2006.01) | |
| *G01N 33/543* | (2006.01) | |
| *G01N 33/58* | (2006.01) | |

(52) U.S. Cl.
CPC ............ *C12Q 1/34* (2013.01); *C12N 9/14* (2013.01); *C12Q 1/002* (2013.01); *C12Q 1/005* (2013.01); *G01N 33/54346* (2013.01); *G01N 33/582* (2013.01)

(58) Field of Classification Search
CPC .......... C12Q 1/34; C12Q 1/005; C12Q 1/002; G01N 33/5434; G01N 33/582; G01N 21/6428; C12N 9/14
See application file for complete search history.

(56) References Cited

U.S. PATENT DOCUMENTS

2012/0178099 A1*  7/2012  Jana .................. B82Y 15/00
                                                      435/7.1

OTHER PUBLICATIONS

Ahn, J.-H., et al., "Label-Free, Single Protein Detection on a Near-Infrared Fluorescent Single-Walled Carbon Nanotube/Protein Microarray Fabricated by Cell-Free Synthesis", Nano Letters, 11(7), (2011), 2743-2752.

Almin, K. E., et al., "Enzymic degradation of polymers. I. Viscometric method for the determination of enzymic activity", Biochim. Biophys. Acta—Enzymol., 139(2), (1967), 238-247.

(Continued)

*Primary Examiner* — Abdullahi Nur
(74) *Attorney, Agent, or Firm* — Schwegman Lundberg & Woessner, P.A.

(57) ABSTRACT

Various embodiments disclosed relate to a sensor assembly probe for determining enzymatic activity. The sensor assembly probe includes one or more fluorescent hydrophobic semi-conductive nanoparticles disposed in an aqueous medium. The assembly further includes an amphiphilic polymer including a substrate for a predetermined enzyme. The amphiphilic polymer coats at least a portion of a surface of the fluorescent hydrophobic semi-conductive nanoparticle.

20 Claims, 11 Drawing Sheets

(56) References Cited

OTHER PUBLICATIONS

Bachilo, S. M., et al., "Structure-Assigned Optical Spectra of Single-Walled Carbon Nanotubes", Science, 298(5602), (2002), 2361-2366.
Boghossian, A., et al., "The chemical dynamics of nanosensors capable of single-molecule detection", J. Chem. Phys. 135, 084124, (2011), 10 pgs.
Chang, E., et al., "Protease-activated quantum dot probes", Biochem. Biophys. Res. Commun., 334(4), (2005), 1317-1321.
Deryugina, E. I., et al., "Matrix metalloproteinases and tumor metastasis", Cancer Metastasis Rev., 25(1), (2006), 9-34.
Dicosimo, R., et al., "Industrial use of immobilized enzymes", Chem. Soc. Rev., 42, (2013), 6437-6474.
Dong, Yi-Hu, et al., "Quorum Sensing and Quorum-Quenching Enzymes", The Journal of Microbiology, 43, Special Issue (No. 5), (2005), 101-109.
Fan, X., et al., "Sensitive optical biosensors for unlabeled targets: a review", Anal. Chim. Acta, 620(1-2), (2008), 8-26.
Fernandes, P., et al., "Enzymes in Food Processing: A Condensed Overview on Strategies for Better Biocatalysts", Enzyme Research, vol. 2010, Article ID 862537, (2010), 19 pgs.
Gill, R., et al., "Fluorescence Resonance Energy Transfer in CdSe/ZnS-DNA Conjugates: Probing Hybridization and DNA Cleavage", J. Phys. Chem. B, 109 (49), (2005), 23715-23719.
Gusakov, A. V., et al., "Comparison of Two Methods for Assaying Reducing Sugars in the Determination of Carbohydrase Activities", International Journal of Analytical Chemistry, vol. 2011, Article ID 283658, (2011), 4 pages.
Heller, D. A., et al., "Optical Detection of DNA Conformational Polymorphism on Single-Walled Carbon Nanotubes", Science, 311(5760), (2006), 508-511.
Heller, D. A., et al., "Peptide secondary structure modulates single-walled carbon nanotube fluorescence as a chaperone sensor for nitroaromatics", Proc. Natl. Acad. Sci. USA, 108(21), (2011), 8544-8549.
Iverson, N. M., et al., "In vivo biosensing via tissue-localizable near-infrared-fluorescent single-walled carbon nanotubes", Nature Nanotechnology, vol. 8, (Nov. 2013), 873-880.
Kim, G. B., et al., "Analysis of Protease Activity Using Quantum Dots and Resonance Energy Transfer", Theranostics, 2(2), (2012), 127-138.
Kim, J.-H., et al., "Single-Molecule Detection of H2O2 Mediating Angiogenic Redox Signaling on Fluorescent Single-Walled Carbon Nanotube Array", ACS Nano, 5(10), (2011), 7848-7857.
Kim, Y.-P., et al., "Bioluminescent nanosensors for protease detection based upon gold nanoparticle-luciferase conjugates", Chemical Communications (Camb), 46(1), (2010), 76-78.
King, B. C., et al., "Arsenal of plant cell wall degrading enzymes reflects host preference among plant pathogenic fungi", Biotechnol Biofuels, 4: 4, (2011), 14 pages.
Kitiyanan, B., et al., "Controlled production of single-wall carbon nanotubes by catalytic decomposition of CO on bimetallic Co—Mo catalysts", Chem. Phys. Lett., 317(3-5), (2000), 497-503.
Kruss, S., et al., "Carbon nanotubes as optical biomedical sensors", Adv. Drug Deliv. Rev., 65(15), (2013), 1933-1950.
Kruss, S., et al., "Neurotransmitter Detection Using Corona Phase Molecular Recognition on Fluorescent Single-Walled Carbon Nanotube Sensors", J. Am. Chem. Soc., 136(2), (2014), 713-724.
Landry, M. P., et al., "Experimental Tools to Study Molecular Recognition within the Nanoparticle Corona", Sensors (Basel), 14(9), (2014), 16196-16211.
Li, S., et al., "Technology Prospecting on Enzymes: Application, Marketing and Engineering", Comput Struct Biotechnol J., 2: e201209017, (Sep. 2012), 11 pages.
Manafi, M., "Fluorogenic and chromogenic enzyme substrates in culture media and identification tests", International Journal of Food Microbiology, 31(1-3), (Aug. 1996), 45-58.
Michalet, X., et al., "Quantum Dots for Live Cells, in Vivo Imaging, and Diagnostics", Science, 307(5709), (2005), 538-544.
Mu, B., et al., "A Structure-Function Relationship for the Optical Modulation of Phenyl Boronic Acid-Grafted, Polyethylene Glycol-Wrapped Single-Walled Carbon Nanotubes", J. Am. Chem. Soc., 134(42), (2012), 17620-17627.
Nelson, J. T., et al., "Mechanism of Immobilized Protein A Binding to Immunoglobulin G on Nanosensor Array Surfaces", Anal. Chem., 87(16), (2015), 8186-8193.
Nummi, M., et al., "Nephelometric and turbidometric assays of cellulase activity", Analytical Biochemistry, 116(1), (Sep. 1981), 133-136.
Olson, B., "Assays for Determination of Protein Concentration", Current Protocols in Protein Science, Chapter 3:Unit 3.4, (2007), pp. 3.4.1-3-4-29.
Ortega, N., et al., "Kinetic behaviour and thermal inactivation of pectinlyase used in food processing", Int. J. Food Sci. Technol, 39(6), (2004), 631-639.
Rapport, M. R., et al., "Correlation of reductimetric and turbidimetric methods for hyaluronidase assay", Journal of Biological Chemistry, 186(2), (1950), 615-623.
Reese, E. T., et al,, "The biological degradation of soluble cellulose derivatives and its relationship to the mechanism of cellulose hydrolysis", J. Bacteriol., 59(4), (1950), 485-497.
Resch-Genger, U., et al., "Quantum dots versus organic dyes as fluorescent labels", Nat Methods, 5(9), 2008), 763-775.
Reuel, N. F., et al,, "Emergent Properties of Nanosensor Arrays: Applications for Monitoring IgG Affinity Distributions, Weakly Affined Hypermannosylation, and Colony Selection for Biomanufacturing", ACS Nano, 7(9), (2013), 7472-7482.
Reuel, N. F., "Three-Dimensional Tracking of Carbon Nanotubes within Living Cells", ACS Nano, 6(6), (2012), 5420-5428.
Reuel, N. F., et al., "Transduction of Glycan-Lectin Binding Using Near-Infrared Fluorescent Single-Walled Carbon Nanotubes for Glycan Profiling", J. Am. Chem. Soc. 133(44), (2011), 17923-17933.
Rivers, D. B., et al., "Limitations of the DNS assay for reducing sugars from saccharified lignocellulosics", Biotechnology and Bioengineering, 26(7), (1984), 800-802.
Sapan, C. V., et al., "Colorimetric protein assay techniques", Biotechnol. Appl. Biochem., 29, (1999), 99-108.
Singh, R., et al., "Microbial enzymes: industrial progress in 21st century", 3 Biotech, 6: 174, (2016), 15 pages.
Smidsrød, O., et al., "Oxidative-reductive depolymerization: a note on the comparison of degradation rates of different polymers by viscosity measurements", Carbohydrate Research, 5(4), (Dec. 1967), 482-485.
Smith, A. M., et al., "Second window for in vivo imaging", Nat Nanotechnol., 4(11), (2009), 710-711.
Tietz, N. W., et al., "Turbidimetric measurement of lipase activity—problems and some solutions", Clin Chem, 33(9), (1987), 1624-1629.
Tzafriri, A. R., et al., "Michaelis-Menten kinetics at high enzyme concentrations", Bull. Math. Biol., 65(6), (2003), 1111-1129.
Uribe, S., "Measuring Solution Viscosity and its Effect on Enzyme Activity", Biol Proced Online, 5(1), (2003), 108-115.
Vorwerk, S., et al., "The role of plant cell wall polysaccharide composition in disease resistance", Trends Plant Sci., 9(4), (2004), 203-209.
Wichmann, O., et al., "A Small-Molecule FRET Probe to Monitor Phospholipase A2 Activity in Cells and Organisms", Angewandte Chemie International Edition, 45(3), (2006), 508-512.
Yao, H., et al., "Quantum Dot/Bioluminescence Resonance Energy Transfer Based Highly Sensitive Detection of Proteases†", Angewandte Chemie International Edition, 46(23), (2007), 4346-4349.
Zhang, J., et al., "Molecular recognition using corona phase complexes made of synthetic polymers adsorbed on carbon nanotubes", 2014 40th Annual Northeast Bioengineering Conference (NEBEC), Apr. 25-27, 2014, (2014), 2 pgs.
Zhang, J., et al., "Single Molecule Detection of Nitric Oxide Enabled by d(AT)15 DNA Adsorbed to Near Infrared Fluorescent Single-Walled Carbon Nanotubes", J. Am. Chem. Soc., 133(3), (2011), 567-581.

\* cited by examiner

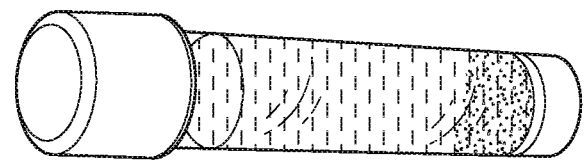
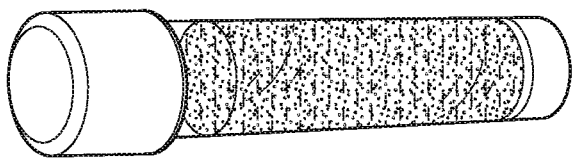
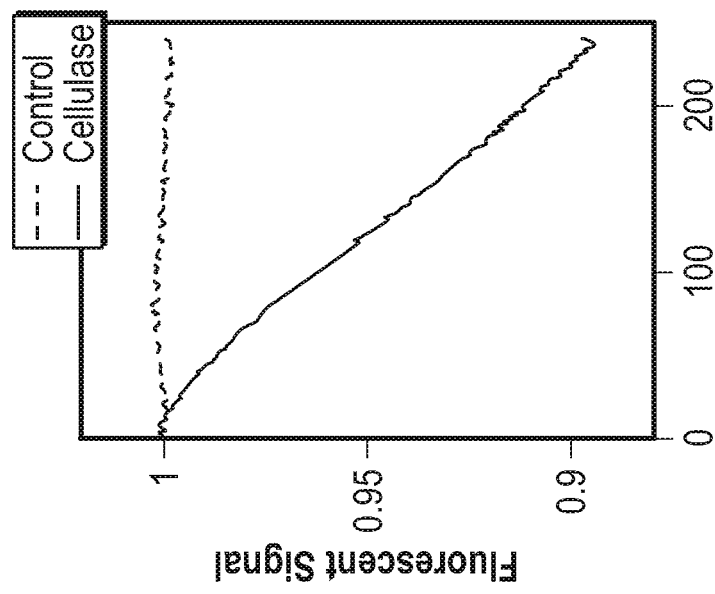
FIG. 2C
FIG. 2B
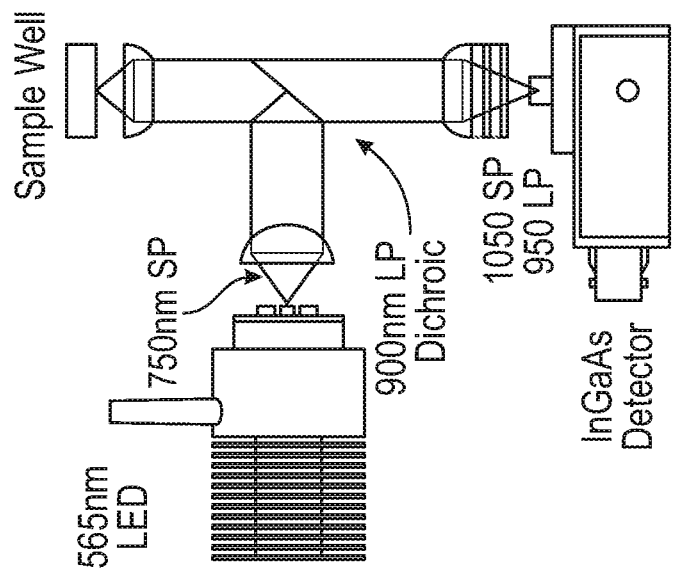
FIG. 2A

OPTICAL NANOSENSORS FOR HYDROLYTIC ENZYME CHARACTERIZATION

CROSS-REFERENCE TO RELATED APPLICATION

This application claims the benefit of priority to U.S. Provisional Patent Application Ser. No. 62/623,593 entitled "OPTICAL NANOSENSORS FOR HYDROLYTIC ENZYME CHARACTERIZATION," filed Jan. 30, 2018, the disclosure of which is incorporated herein in its entirety by reference.

BACKGROUND

Determining the presence and activity of an enzyme can be useful in many different contexts. In some applications, this can be done indirectly by detecting the presence of byproducts of the reaction between an enzyme and substrate. Indirect detection can be unreliable and potentially expensive. It may, therefore, be desirable to develop improved detection methods and assemblies.

SUMMARY OF THE DISCLOSURE

Various embodiments disclosed relate to a sensor assembly probe for determining enzymatic activity. The sensor assembly probe includes one or more fluorescent hydrophobic semi-conductive nanoparticles disposed in an aqueous medium. The assembly further includes an amphiphilic polymer including a substrate for a predetermined enzyme. The amphiphilic polymer coats at least a portion of a surface of the fluorescent hydrophobic semi-conductive nanoparticle.

Various further embodiments disclosed relate to a method of using a sensor assembly probe. The sensor assembly probe includes one or more fluorescent hydrophobic semi-conductive nanoparticles disposed in an aqueous medium. The assembly further includes an amphiphilic polymer including a substrate for a predetermined enzyme. The amphiphilic polymer coats at least a portion of a surface of the fluorescent hydrophobic semi-conductive nanoparticle. The method includes providing or receiving at least one of the probe and the predetermined enzyme. The method further includes measuring a first fluorescent frequency emission of the probe. The method further includes contacting the probe and the predetermined enzyme. The method further includes measuring a second fluorescent frequency emission of the probe. The second fluorescent frequency emission is less than the first fluorescent frequency emission and indicates that at least a portion the substrate has reacted with the predetermined enzyme.

Various further embodiments disclosed relate to a method of making a sensor assembly probe. The sensor assembly probe includes one or more fluorescent hydrophobic semi-conductive nanoparticles disposed in an aqueous medium. The assembly further includes an amphiphilic polymer including a substrate for a predetermined enzyme. The amphiphilic polymer coats at least a portion of a surface of the fluorescent hydrophobic semi-conductive nanoparticle. The method includes dispersing the fluorescent hydrophobic semi-conductive nanoparticle and the amphiphilic polymer in an aqueous medium. The method further includes mixing the fluorescent hydrophobic semi-conductive nanoparticle and the amphiphilic polymer, to form the sensor assembly.

There are many advantages associated with the assemblies and methods disclosed herein, some of which are unexpected. For example, according to various embodiments, the assembly can be easily and rapidly synthesized and detect the presence of an enzyme and depletion of an enzyme substrate in real time. According to various embodiments, the assembly is versatile, for example, it can screen different types of substrate and enzyme combinations. According to various embodiments, depletion of substrate can be correlated with signal change to predict quantitative rate constants. According to various further embodiments, comparison with an established colorimetric assay can demonstrate high performance in complex, otherwise-difficult samples. According to various further embodiments, the assemblies and methods disclosed herein can be used to rapidly track changes in enzyme activity to monitor damage or to perform optimization operations.

According to further embodiments, the assembly's versatility, compact size scale, and penetrating near infrared spectral window can make it suitable for a range of enzyme-related applications. According to further embodiments, the assemblies and methods disclosed herein may be suitable, for example, in industrial biotechnology by offering speed and simplicity enhancement to routine optimization studies where new mutant hydrolase enzymes are screened to determine optimal operating conditions. According to various embodiments, for example in medical applications, the methods and assemblies may be used for in vivo zymography, or the tracking of temporal and spatial dynamics of health-related enzymes such as matrix metalloproteinases (MMPs) from tumors. According to various embodiments, for example, in drug development, the assemblies and methods may be used in the design and screening of hydrolase inhibitors. According to various embodiments, for example, in food production, the assemblies and methods may be used to test and design cost-effective immobilization strategies for hydrolases in routine processing such as saccharification. According to various embodiments, the assemblies and methods can be modified to increase portability, sensitivity, and to reduce cost. Furthermore, according to various embodiments, sensor stability, sensitivity, and selectivity can be further optimized by modifying sensor manufacturing conditions and wrapping properties of the amphiphilic polymer to the nanoparticles.

BRIEF DESCRIPTION OF THE FIGURES

The drawings illustrate generally, by way of example, but not by way of limitation, various embodiments discussed in the present document.

FIG. 2A is a schematic diagram of a near infrared (nIR) fluorometer, in accordance with various embodiments.

FIG. 2B is a graph showing normalized single walled carbon nanotube (SWNT) sensor fluorescence signal versus time for water addition (control) and cellulase (response), in accordance with various embodiments.

FIG. 2C is a perspective view and shows on the left side a sample of carboxymethyl cellulose (CMC)-wrapped nanotubes where an amphiphilic substrate attached an individual nanotube is not consumed and on the right shows nanotubes where the amphiphilic substrate is at least partially consumed, in accordance with various embodiments.

DETAILED DESCRIPTION

Figure 1:
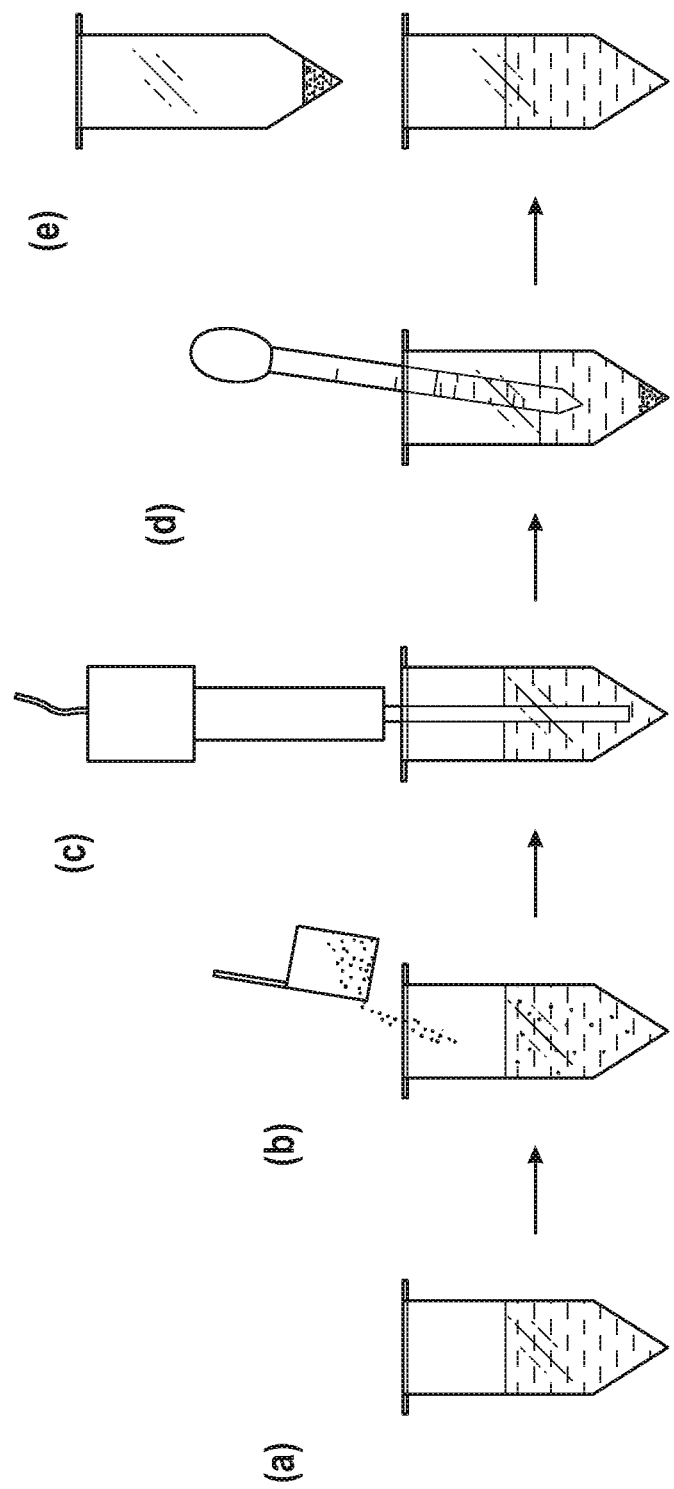
FIG. 1 is a schematic depiction of a procedure for synthesizing a sensor, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

This disclosure is directed towards various embodiments of a sensor assembly probe. The sensor assembly probe can be used for determining enzymatic activity. The sensor assembly can include one or more fluorescent hydrophobic semi-conductive nanoparticles disposed in an aqueous medium. The sensor assembly probe further includes an amphiphilic polymer. The amphiphilic polymer coats at least a portion of a surface of the fluorescent hydrophobic semi-conductive nanoparticle. The amphiphilic polymer can be a substrate for a predetermined enzyme.

In operation, the nanoparticles have a detectable fluorescent emission when dispersed in the aqueous medium. The nanoparticles are hydrophobic by nature but are solubilized by the amphiphilic polymer coated thereon. Upon contact with the predetermined enzyme the amphiphilic polymer, which is a substrate of the enzyme, is consumed. Upon consumption, the hydrophobic nanoparticles in the aqueous medium aggregate and the fluorescence of the nanoparticles is quenched, thus indicating the presence of the enzyme.

The nanoparticles can include any suitable material. Examples of suitable materials can include a ceramic material (e.g., aluminum oxide or copper(II) oxide), a polymer, a glass-ceramic, a composite, a metal carbide (e.g., SiC), a nitride (e.g., aluminum nitride, silicon nitride), a metal (e.g., Al, Cu, Au, Ag), a non-metal (e.g., graphite and carbon). The nanoparticle can have any suitable morphology. For example, the morphology of the nanoparticle can be chosen from a nanosphere, a nanorod, a nanofiber, a nanotube, a nanostar, a nanocup, or combinations thereof. At least one of a length, width, and diameter of the nanoparticle is in a range of from about 1 nm to about 10,000 nm, about 1 nm to about 100 nm, about 10 nm to about 50 nm, about 100 nm to about 2,500 nm, about 2,500 nm to about 10.000 nm, or less than, equal to, or greater than about 1 nm, 25, 50, 100, 500, 1,000, 1,500, 2,000, 2,500, 3,000, 3,500, 4,000, 4,500, 5,000, 5,500, 6,000, 6,500, 7,000, 7,500, 8,000, 8,500, 9,000, 9,500, or about 10.000 nm. Generally, nanoparticles in which at least one of a length, width, and diameter of the nanoparticle is in a range of from about 1 nm to about 100 nm are classified as ultrafine nanoparticles. Generally, nanoparticles in which at least one of a length, width, and diameter of the nanoparticle is in a range of from about 100 nm to about 2.500 nm are classified as fine nanoparticles. Generally, nanoparticles in which at least one of a length, width, and diameter of the nanoparticle is in a range of from about 2.500 nm to about 10,000 nm are classified as coarse nanoparticles. The morphology of the nanoparticles can be uniform.

The sensor assembly probe can include a plurality of the nanoparticles. Respective individual nanoparticles can have at least one of substantially the same morphology, substantially the same dimensions, and have substantially the same composition. Alternatively, the respective individual nanoparticles can differ in at least one of their morphologies, dimensions, and compositions. The plurality of nanoparticles can be heterogeneously or homogenously distributed in the aqueous medium.

When at least one nanoparticle is dispersed in the aqueous medium (e.g., free of agglomeration with another nanoparticle) the nanoparticle fluoresces. In some embodiments, the nanoparticle can fluoresce at wavelengths ranging from about 800 nm to about 1500 nm, 950 nm to about 1100 nm, or less than, equal to, or greater than about 800, 810, 820, 830, 840, 850, 860, 870, 880, 890, 900, 910, 920, 930, 940, 950, 960, 970, 980, 990, 1000, 1100, 1200, 1300, 1400, or about 1500 nm. In embodiments where the sensor assembly probe includes a plurality of nanoparticles, respective nanoparticles can fluoresce at substantially the same frequency.

In other embodiments where the sensor assembly includes a plurality of nanoparticles, respective nanoparticles can fluoresce at different frequencies. For example, the respective fluorescent signals emitted by the first fluorescent hydrophobic semi-conductive nanoparticle and the second fluorescent hydrophobic semi-conductive nanoparticle have intensities of fluorescence that differ by about 0 to 100%, about 0 to 20% or less than, equal to, or greater than about 0%, 5, 10, 15, 20, 25, 30, 35, 40, 45, 50, 55, 60, 65, 70, 75, 80, 85, 90, 95, or 100%.

The amphiphilic polymer can be any suitable polymer that can act as a substrate for the predetermined enzyme. In some embodiments, the amphiphilic polymer can be a protein, a peptide, or a mixture thereof. Examples of suitable amphiphilic polymers include those with a bond that is hydrolyzable by the predetermined enzyme. Examples of such bonds can include an ester bond, a glycosylic bond, an ether bond, a peptide bond, an acid anhydride bond, a halide bond, a phosphorous-sulfur bond, a sulfur-sulfur bond, a carbon-phosphorous bond, a carbon-sulfur bond, or a combination thereof. Further suitable amphiphilic polymers include those that have at least one functional group or moiety that is capable of being oxidized. Examples of amphiphilic polymers include a bovine serum albumin, citrus pectin, carboxymethyl cellulose, a polyphenol (e.g., lignin), a lipid (e.g., a phospholipid), a lignosulfonic acid, a cellulose or a derivative (e.g., carboxymethyl cellulose) or a mixture thereof. Specific amphiphilic polymers can include hyaluronan, collagen, gelatin, phosphatidylcholine, or a combination thereof.

The sensor assembly probe can include a plurality of amphiphilic polymers. Respective amphiphilic polymers can differ by composition, weight-average-molecular weight or a combination thereof. The respective amphiphilic polymers can further be substrates of the same enzyme or different enzymes. In embodiments where the sensor assembly probe includes different amphiphilic polymers, the respective polymers can each coat a portion of a first nanoparticle or can coat respective different nanoparticles.

The extent to which an amphiphilic polymer coats the nanoparticle can be tuned to any suitable degree. For example, the amphiphilic polymer can coat from about 20% to about 100% of surface area of the nanoparticle, about 50% surface area to about 90% surface area, about 90% surface area to about 100% surface area, or less than, equal to, or greater than about 20%, 25, 30, 35, 40, 45, 50, 55, 60, 65, 70, 75, 80, 85, 90, 95, or 100% surface area.

The amphiphilic polymer itself can be the substrate for the enzyme. In other embodiments, however, the amphiphilic polymer may not be the substrate and instead the substrate may be grafted to the polymer. In some embodiments, the grafted substrate can include a functional group to the substrate.

The predetermined enzyme in the sensor probe assembly can be any suitable enzyme. The enzyme is selected to react with the substrate amphiphilic polymer. The sensor assembly probe can include more than one types of enzyme. In embodiments that include more than one enzyme, the enzymes can be the same enzyme or a mixture of different enzymes. Where different enzymes are present in the assembly, the different enzymes can be adapted to react with different amphiphilic polymers. The amphiphilic polymer that a particular enzyme reacts with may be present in the assembly or may not be present in the assembly.

The predetermined enzyme or enzymes may belong to any class of enzymes. For example, the enzyme or enzymes may be classified as a hydrolase (alternatively known as an EC 3 enzyme). The hydrolase can be classified by the bond it acts upon. For example, the hydrolase can be chosen from an esterase, nuclease, phosphodiesterase, lipase, a phospholipase, phosphatase, DNA glycosylase, glycoside hydrolase, proteases, peptidase, acid anhydride hydrolase, helicase. GTPase, a hyaluronidase, or mixtures thereof. In some embodiments, the predetermined enzyme or enzymes can be an oxidative enzyme.

The sensor assembly can be used according to any suitable method. According to various embodiments, the method can include dispensing the nanoparticles that are at least partially coated with the amphiphilic polymer in an aqueous medium. The amphiphilic polymer serves as a substrate for the predetermined enzyme but also solubilizes the nanoparticles. When the nanoparticles are solubilized, they produce a fluorescent emission. The initial fluorescent is measured. In some embodiments where the assembly includes a mixture of nanoparticles that produce different fluorescent emissions, multiple emissions may be measured.

The enzyme or mixture of enzymes are then contacted with the nanoparticles. If an enzyme is associated with a particular substrate, the substrate will be consumed and the fluorescent emission of the nanoparticle to which the substrate is attached will be quenched. Thus, a measured second fluorescent emission will have a smaller intensity than the first fluorescent emission or there will be no fluorescent emission.

Measuring a second fluorescent emission that is less than the first fluorescent emission confirms the presence of a predetermined enzyme. In embodiments where nanoparticles having different fluorescent emissions and different substrates attached thereto are present, a decrease in the emission in one or both of the nanoparticles can indicate the presence of two different predetermined enzymes. In this manner, the presence of one or more enzymes in a mixture of enzymes or another constituent of a solution can be confirmed. Additionally, the rate of reaction between the predetermined enzyme and a substrate can be determined by monitoring the rate at which the fluorescent emission intensity decreases.

The sensor assembly can be formed according to any suitable method. For example, the assembly can be formed by dispersing the nanoparticles in an aqueous medium. The nanoparticles can then be mixed with the amphiphilic polymers. Mixing can be accomplished for example through sonication.

EXAMPLES

Various embodiments of the present disclosure can be better understood by reference to the following Examples which are offered by way of illustration. The present disclosure is not limited to the Examples given herein.

Example 1. Hydrolytic Enzymes

Hydrolytic enzymes were examined due to their industrial impact and biological implications. The inventors sought to design, a versatile single walled carbon nanotube (SWNT)-based sensor that is facile to produce and measure. The hydrolytic enzyme substrate was rendered as an amphiphilic polymer which was used to solubilize the hydrophobic nanotubes. When the target enzyme degraded the wrapping, SWNT fluorescent signal is quenched due to increased solvent accessibility and nanotube aggregation, allowing quantitative measurement of hydrolytic enzyme activity. Using (6,5) chiral SWNT suspended with polypeptides and polysaccharides, turnover frequencies were estimated for cellulase, pectinase, and bacterial protease. Responses were recorded for concentrations as low as 5 fM using a well-characterized protease, Proteinase K. A trypsin-based plate reader assay is used to correlate these rates with standard techniques. Furthermore, the effect of freeze-thaw cycles and elevated temperature on enzyme activity were measured, suggesting freezing to have minimal impact even after 10 cycles and heating to be detrimental above 60° C. Finally, rapid optimization of enzyme operating conditions was demonstrated by generating a response surface of cellulase activity with respect to temperature and pH to determine optimal conditions within 2 hours of serial scans.

Hydrolytic enzymes play important roles in natural biological systems and therefore are significant designed products for modern biotechnological processes. The enzymes studied were classified together (Enzyme Class 3) based on their ability to catalyze the hydrolysis of chemical bonds; sub-classifications reveal the breadth of activities these enzymes have developed, cleaving the following bonds: esters (EC 3.1), glycosylic (EC 3.2), ether (EC 3.3), peptides (EC 3.4), C—N other than peptides (EC 3.5), acid anhydrides (EC 3.6). C—C (EC 3.7), halide (EC 3.8), P—N (EC 3.9). S—N (EC 3.10), C—P (EC 3.11), S—S (EC 3.12), and C—S (EC 3.13). In nature, these enzymes are the recyclers of bulk materials, breaking down proteins, carbohydrates, and fats into their constitutive parts to make available smaller building blocks for new biological assembly. Hydrolytic enzymes also have natural, prominent roles in disease. For plants, pathogenic bacteria and pests can excrete enzymes to breakdown the recalcitrant cell walls to help their invasion. In cancer, tumors secrete a class of matrix metalloproteinases (MMP) that are responsible for reconfiguring healthy tissue into a permeable matrix that allows for tumor growth and metastasis. Engineered product examples of hydrolytic enzymes include the use of hydrolases in detergent to aid in stain removal, animal feed to aid in digestion, paper pulp preparation, and food processing such as cheese making, leather tanning, biofuels, juice clarification, baking, brewing, sugaring, and meat processing. For these engineered enzyme applications, an entire industry has grown around the optimization and design of more stable and efficient enzymes for process use, with an overall industrial enzyme market size of $4.2 billion in 2014 and predicted growth to $6.2 billion in 2020 with hydrolytic enzymes accounting for 75% of these products.

Although hydrolytic enzyme function and design has improved, one potentially limiting factor in the study and design of these catalysts may be the ability to measure their activity and selectivity in real time with a modular tool. Specialized probes and techniques have been previously developed to screen hydrolytic activity, including FRET-based probes, chromogenic substrate analogs, indirect measurement of substrate by correlations, and single-point colorimetric assays (Table 1).

TABLE 1

Methods of Detecting Hydrolytic Activity

| Method | Transducer | Strengths | Limitations |
| --- | --- | --- | --- |
| FRET and BRET-Based Probes | Organic dyes | Established linking chemistry protocols, Discrete fluorescent peaks[1] | Photobleaching, Some toxic dyes |
| | Quantum dots | High quantum yield in near-infrared window, High reliability and sensitivity | "Blinking," Few linking chemistry protocols available, Large molecular size, Cytotoxicity, Low FRET |

TABLE 1-continued

Methods of Detecting Hydrolytic Activity

| Method | Transducer | Strengths | Limitations |
|---|---|---|---|
| | Luciferase | Stability in biological media, High sensitivity | Efficiency Must be paired with fluorophore, Requires luciferase substrate |
| Substrate Structural Analogs | Organic chromogenic substrates | Easily implemented, minimal preparation | Relatively low sensitivity |
| Indirect measurement of substrate | Viscosimetry | Directly applicable to multiple polymers | Nonlinear response, Sensitive to matrix elements |
| | Turbidimetry | Functional for immiscible or insoluble reagents or products | Other causes of turbidity, Nonlinear short-term response, Single-point nephelometric measurements |
| Single-point assays | Colorimetric or amperometric product assay | Well-established | Time-intensive colorimetric assays, Variable linear dynamic range, Susceptible to interference |

To potentially overcome the limitations of other optical sensors, namely the signal quality and synthesis complexity, single walled carbon nanotubes (SWNT) were used as a fluorescent transducer, offering high assay sensitivity and the advantage of a near infrared emission window which more effectively penetrates complex samples.

Semi-conducting SWNT are naturally fluorescent due to their unique 1-D, energy of states distribution. The fluorescence of the nanotube is sensitive to changes in the SWNT surface dielectric environment. This sensitivity has been exploited to design sensors for small molecules, sugars, metabolites. DNA, proteins, and glycans. Furthermore, the near infrared fluorescence of SWNTs are very photostable with demonstrated in vivo detection on month-to-year timeframes. The quantitative detail of these sensors can map large ensemble kinetic distributions all the way down to single molecule binding kinetics. Not all of the transductions systems provided for optical SWNT sensors are straightforward, but the most recent advances simply exploit the surface sensitivity by binding in the nanotube 'corona' or wrapped polymer phase.

Example 2. Results and Discussion

Example 2.1. Hydrolytic Enzyme Sensors (6,5)-chiral SWNT (diameter=0.76 nm, excitation=567 nm, emission=975 nm) were chosen as the sensor backbone due to their stable near-infrared fluorescence and ease of production by Co—Mo catalysts. The hydrophobic SWNT were suspended in water by wrapping them with amphiphilic, macromolecular substrates. SWNT were dispersed by sonication in the presence of target enzyme substrate and recovered as supernatant after centrifugation. This is shown in FIG. 1, which shows a sensor synthesis procedure. At operation (a) substrate is dissolved in water. At operation (b) SWNT are added to substrate solution. At operation (c) the mixture is sonicated. At operation (d) the mixture is then centrifuged, and the supernatant is extracted, leaving, at operation (e), wrapped nanotube solution and pellet.

While nanotubes may be suspended best with an amphiphilic wrapping, semi-stable suspensions were also possible with substrates that lacked any obvious hydrophobic moiety, such as pectin; however, such wrappings tended to increase variability of the sensor response. Unlike other complex hydrolytic enzyme activity probes, manufacture of each, new SWNT sensor was straightforward, with complete synthesis in less than one hour. The absence of linking chemistry made this a highly modular assay. To demonstrate the modularity, sensors were made with a variety of enzyme-substrate pairs to show transduction of protein, oligosaccharide, and polysaccharide hydrolysis.

To interrogate the SWNT sensor, a new low-cost, open source detector was developed. An optical sensor can only find utility if its requisite illumination source and detector are on the size and cost scale of the intended application. In this case, the widespread use of hydrolytic enzymes as agricultural and industrial catalysts as an application does not support the traditional inverted microscope coupled to high cost lasers and detectors. The reader designed for this Example was an improved model from previous efforts to create portable SWNT detection. The advances have increased the signal to noise quality and provide a price point below $2500.

Figure 2D:
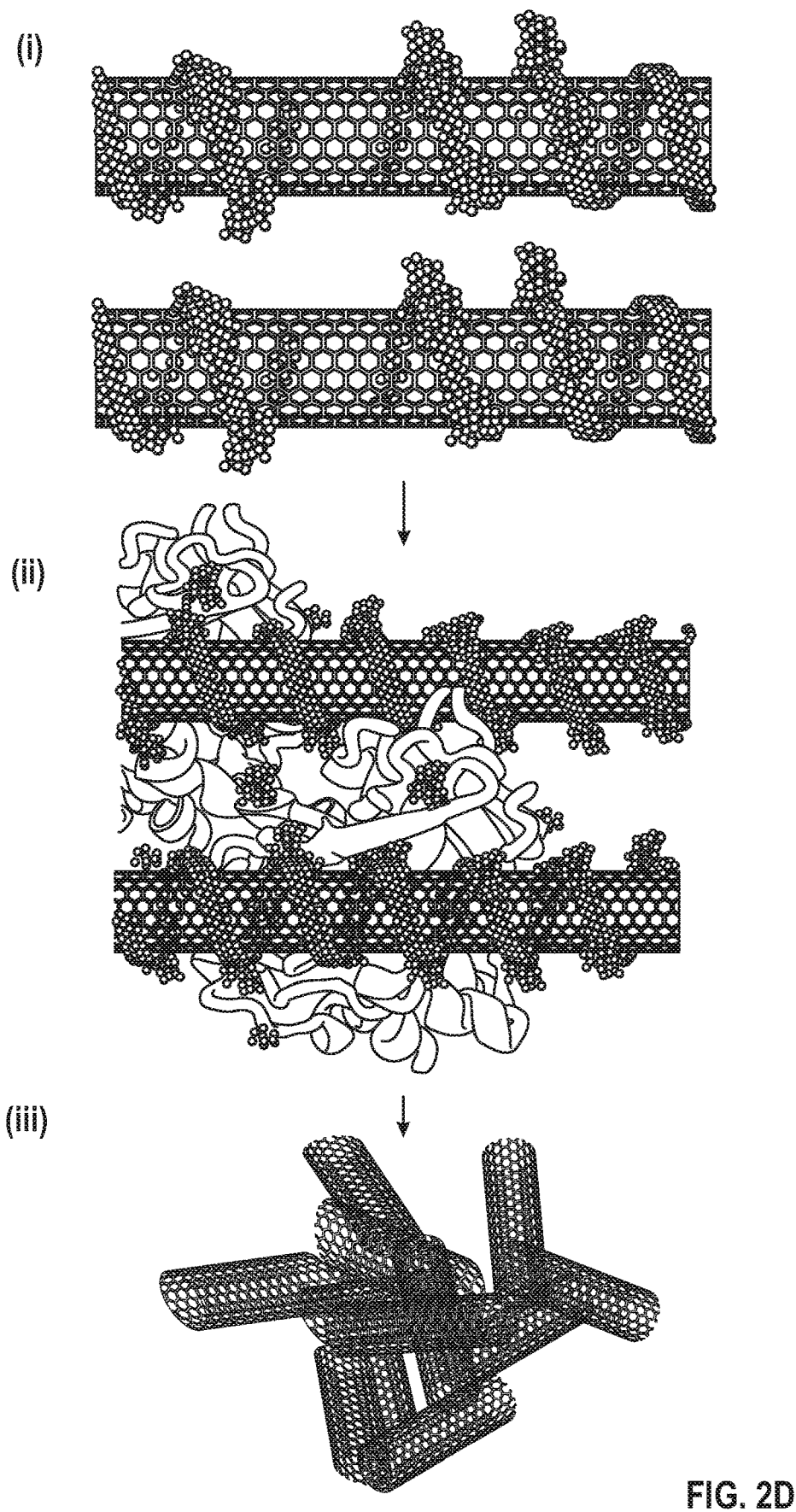
FIG. 2D is a schematic diagram showing a mechanism of sensing using the carboxymethyl cellulose (CMC)-wrapped nanotubes, in accordance with various embodiments.

FIGS. 2A-2D show a sensor device, data, nanotubes, and a proposed mechanism of using the sensor assembly. As generally shown FIG. 2A is a schematic of low cost nIR fluorimeter. FIG. 2B shows normalized SWNT sensor fluorescence signal versus time for water addition (control) and cellulase (response) where the fluorescence signal decreases as the cellulase consumes the substrate. FIG. 2C, on the left shows a sample of carboxymethyl cellulose (CMC)-wrapped nanotubes where the amphiphilic substrate is not consumed and on the right shows nanotubes where the substrate is at least partially consumed and the nanotubes fall out of solution as an agglomerate and settle at bottom. FIG. 2D shows a proposed mechanism of sensing. As shown at operation (i), nanotubes are solubilized by amphiphilic polymer and nanotubes fluoresce. As shown at operation (ii), wrapping is removed due to enzyme hydrolysis. As shown at operation (iii) nanotubes agglomerate causing quenched signal.

As shown in FIG. 2, the reader uses a 565 nm LED diode as an excitation source and an InGaAs amplified avalanche photodetector to measure emission. The detector voltage signal (0-10V) is halved in a custom voltage divider and recorded digitally at high resolution via a 16-bit analog to digital converter coupled to a low cost single board computer.

Hydrolytic activity was measured by adding a small volume of concentrated enzyme solution to the sensor solution and recording decrease to fluorescent signal with respect to time. After decomposition of the wrapping, SWNT were rendered insoluble in water, causing them to agglomerate. While decrease in fluorescence signal was believed to have been caused by a self-quenching effect, it may also be influenced by a dielectric shift caused by exposure of the nanotube surface directly to water. Tests of fluorescent sensors immobilized on an agarose surface still show the quenching event to be possible if the nanotubes are at high enough concentration to have proximal neighbors.

Conversion was determined as a function of signal change, which was normalized after completion of reaction according to Equation (1):

$$X_S = 1 - \frac{I - I_E}{I_0 - I_E} \quad (1)$$

Where $X_s$ is the observed substrate conversion. I is the fluorescent signal intensity, $I_o$ is the starting intensity, $I_E$ is the final, steady-state intensity measured when signal stabilized (1-3 h incubation). This normalization inverts the decreasing, quenched signal response into a positive response. The normalized data was then smoothed by Fourier. While steady-state fluorescence signal was consistent among individual enzymes, it varied among different enzyme types. For example, fluorescence of casein-wrapped SWNT reached background levels after proteolysis by bacterial protease whereas (CMC)-wrapped SWNT remained at higher fluorescence values, likely due to cellulase's inability to hydrolyze carboxymethyl-substituted monomers. These differences likely resulted from the enzyme's inability to completely digest a fraction of the suspended SWNT. It was also possible that, while SWNT are rendered insoluble, remnant substrate wrappings could also have prevented direct contact among SWNT, decreasing FRET efficiency and limiting the quenching effect. In each assay the end fluorescence ($I_E$) was experimentally acquired for use in data normalization. After normalization, comparisons could be made between experiments and kinetic parameters could be determined.

Example 2.2. Sensor Characterization

Sensor agglomeration was observed at the microscale by Atomic Force Microscopy (AFM) scanning. Lysozyme-wrapped SWNT, although exhibiting poor signal stability, were selected for the distinct SWNT visible on scans. After digestion by subtilisin, the SWNT were dwarfed by large agglomerates. Similar tests with Bovine Serum Albumin (BSA)-wrapped SWNT (yielded tendril-like agglomerations after digestion. The size of the agglomerations suggested that complete digestion of globular substrates was not necessary for transduction. Signal quenching could be achieved by the removal of hydrophilic moieties.

Example 2.3. Determining Kinetic Terms

Figure 3A:
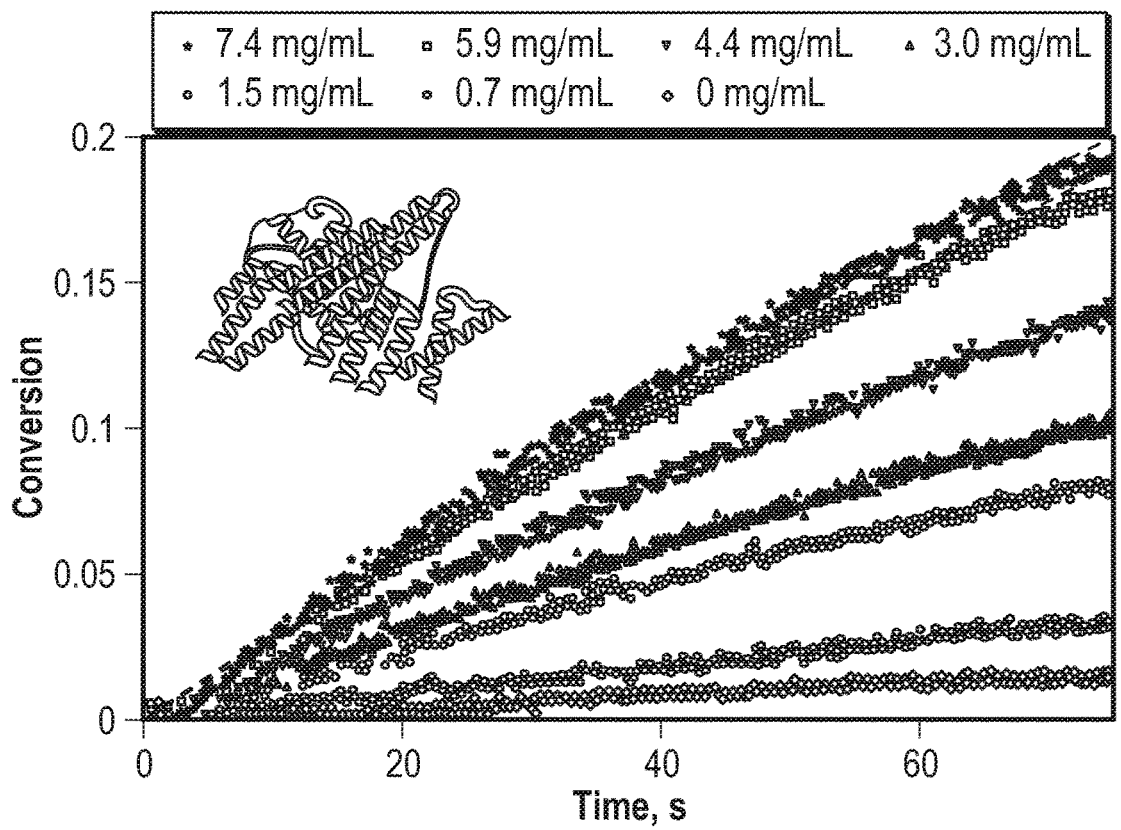
FIG. 3A is a graph showing observed conversion profiles of various concentrations of bovine serum albumin in the presence of bacterial protease over time, in accordance with various embodiments.
Figure 3B:
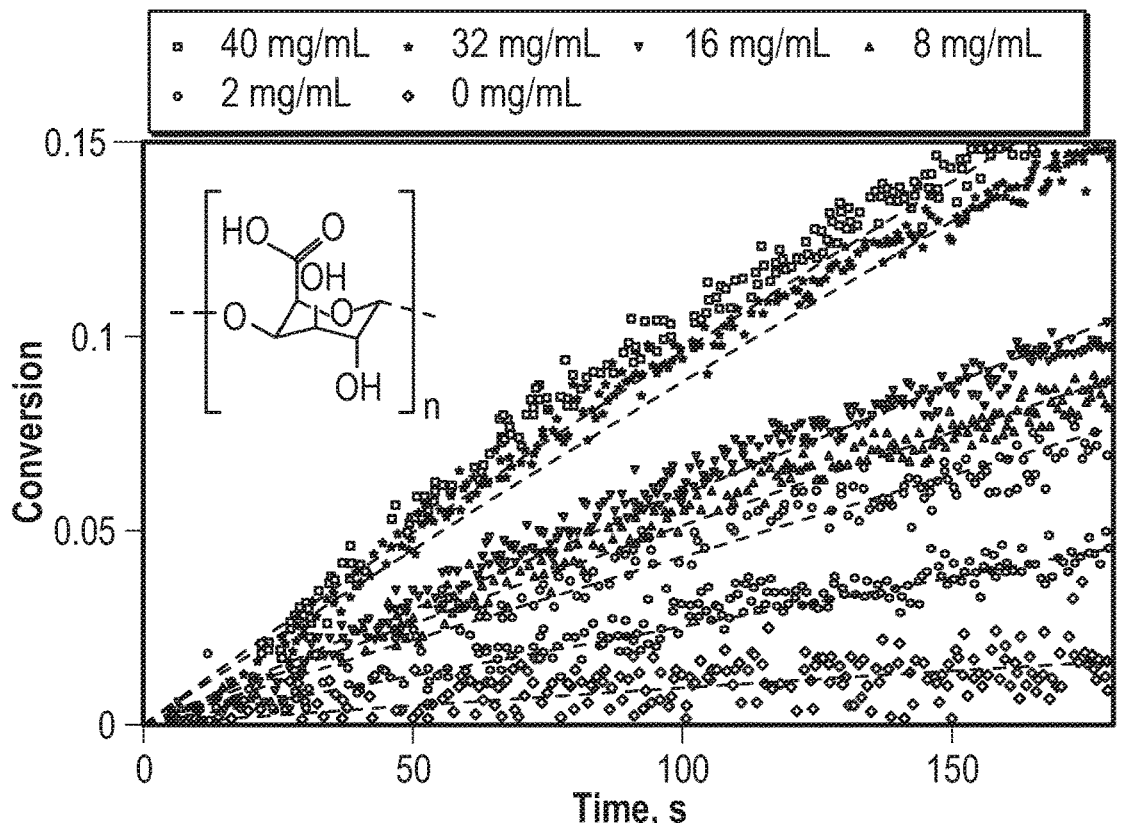
FIG. 3B is a graph showing observed conversion profiles of various concentrations of pectin in the presence of pectinase over time, in accordance with various embodiments.
Figure 3C:
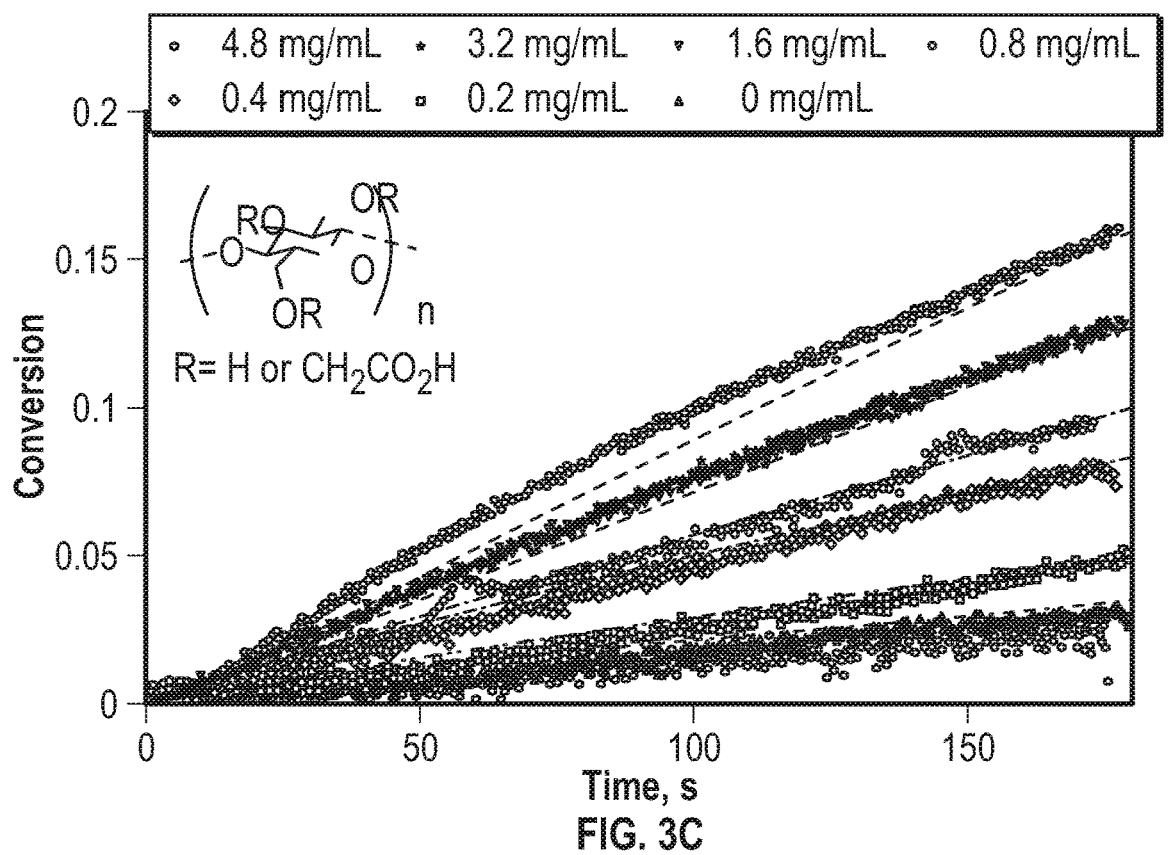
FIG. 3C is a graph showing observed conversion profiles of various concentrations of carboxymethyl cellulose (CMC) in the presence of cellulase over time, in accordance with various embodiments.
Figure 3D:
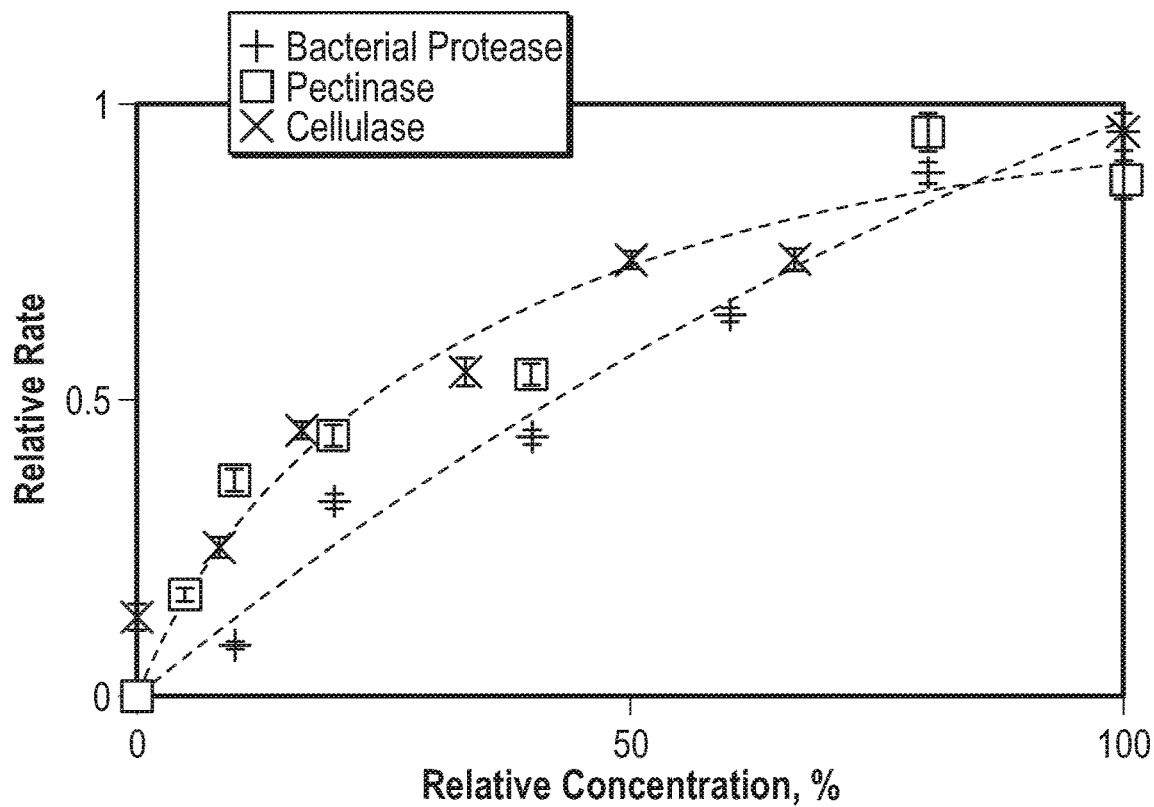
FIG. 3D is a graph showing rate versus concentration pattern in enzymes, in accordance with various embodiments.

To determine kinetic parameters, sensor responses were obtained at a range of enzyme concentrations. FIGS. 3A-3D shows observed conversion profiles at different enzyme concentrations. A positive correlation between rate of signal change and enzyme concentration was observed for bacterial protease to BSA, pectinase to pectin, and cellulase to CMC (FIGS. 3A-3C). The responses appeared to fit with first-order, substrate-limited enzyme kinetics. The relative rates from each experiment were determined based on fitted models and these were plotted against the enzyme concentration (FIG. 3D). Thus, the limiting regime was immediately apparent in the shape of the response.

Kinetic parameters, or observed rate constants, were fit to the relative rate vs. enzyme concentration data (dotted lines in FIG. 3D). For a substrate-limited response, substrate concentration must be redefined as a sum of comparable free and enzyme-bound quantities as shown in Equation (2):

$$[S]_T = [S] + [ES] \quad (2)$$

Where $[S]_T$ is the total substrate concentration, $[S]$ is the unbound substrate concentration, and $[ES]$ is the enzyme-bound substrate concentration. Applying this balance, the rate of substrate consumption may be approximated by Equation (3):

$$\frac{d[S]_T}{dt} = -\frac{k_{cat}[E]_T[S]_T}{K_M + [E]_T + [S]_T} \quad (3)$$

Where t is time, k, is turnover frequency, $[E]T$ is the total enzyme concentration, Km is the Menten constant. Assuming substrate concentration in the denominator to be negligible, observed first order rate constants could be fitted to the Equation (4):

$$\frac{d[S]_T}{dt} = -\frac{k_{cat}[E]_T[S]_T}{K_M + [E]_T} \quad (4)$$

With tests at multiple enzyme concentrations, turnover frequencies were determined. High variability of calculated constants (Table 2) may be associated with inconsistencies in running this assay by hand, such as the pipetting of enzyme solutions and manual positioning of samples over the detection apparatus, which will be mitigated by subsequent automation.

TABLE 2

Kinetic Constants of Crude Enzyme Mixes

| Enzyme-Substrate | Turnover Rate ($s^{-1}$), 95% Confidence |
| --- | --- |
| Bacterial Protease-BSA | $3.785 \pm 2.495 \times 10^{-3}$ |
| Pectinase-Pectin | $1.080 \pm 0.476 \times 10^{-3}$ |
| Cellulase-CMC | $2.354 \pm 0.391 \times 10^{-3}$ |

Example 2.4. Establishing Detection Limit

The detection limit was established with Proteinase K, a subtilisin-like protease selected for its stable and well-characterized activity. Within 5 minutes, signal changes were measurable at enzyme concentrations as low as 500 nM. When incubated for 24-29 h. the sensors yielded a statistically significant response with enzyme concentrations as low as 5 fM. Longer assay times for low concentration enzyme characterization would be acceptable with an automated scanning apparatus where many tests could be conducted in parallel.

Example 2.5. Benchmarking Sensors with an Established Assay

Figure 4B:
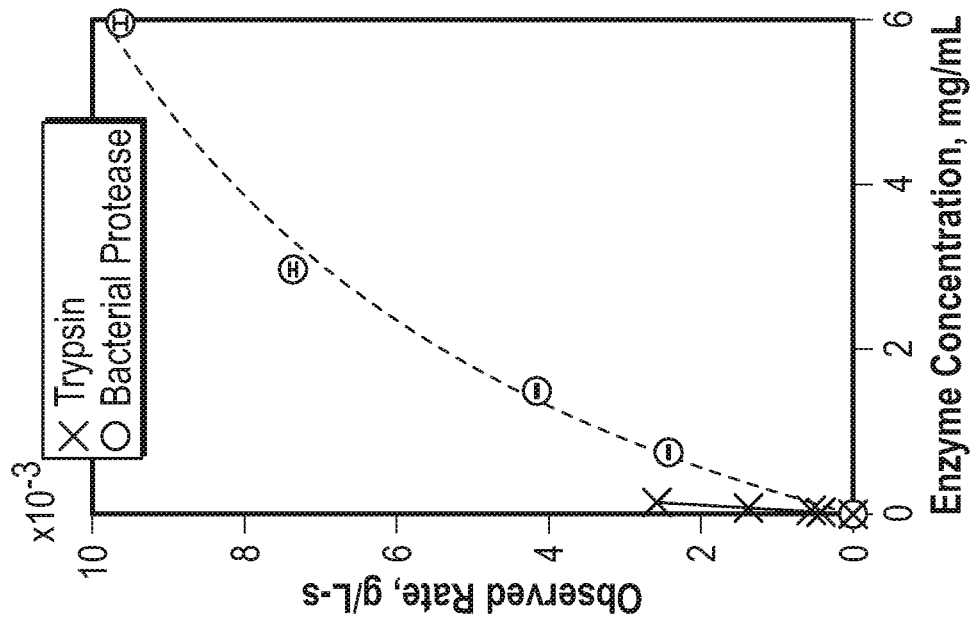
FIG. 4B is a graph showing subtilisin activity compared to a trypsin standard curve on a semi-log plot using the Pierce colorimetric assay, in accordance with various embodiments.
Figure 4A:
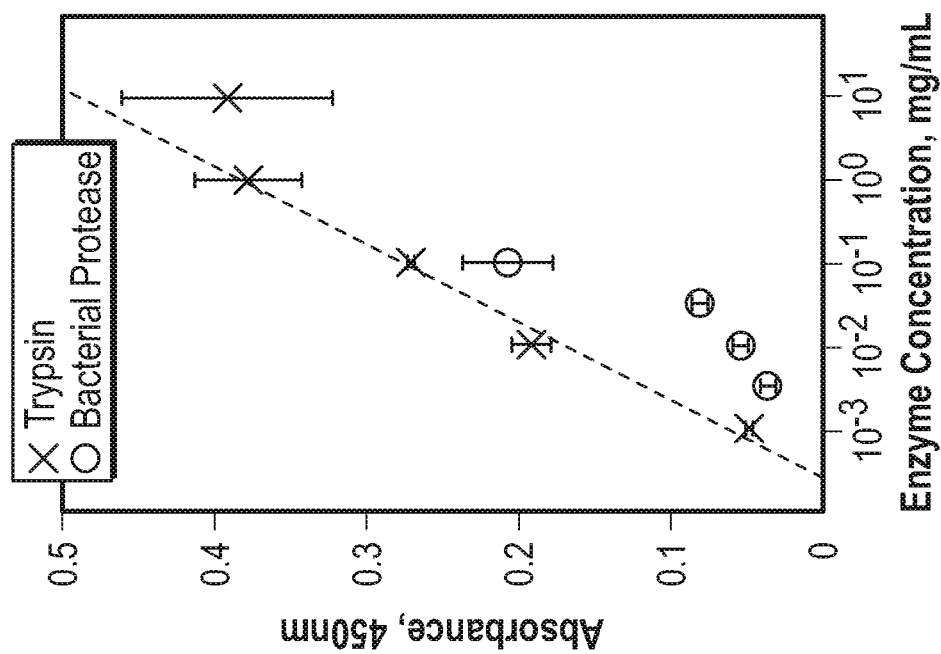
FIG. 4A is a graph showing protease activity fit to a standard curve on a semi-log plot using the Pierce colorimetric assay, in accordance with various embodiments.

To confirm utility of these hydrolytic enzyme sensors, the fluorescent assay was compared to an established colorimetric assay. As shown in FIG. 4A, protease activity was fit to a standard curve on a semi-log plot using the Pierce colorimetric assay. Error increased greatly with increased sample concentrations until responses deviated from linear behavior. In FIG. 4B crude subtilisin samples were compared to a trypsin standard curve. Protease activity was compared to the same trypsin standard using the fluorescent assay. Relative error is comparatively small at high enzyme concentrations. The Pierce colorimetric protease assay kit was used to detect hydrolytic activity of a crude bacterial protease sample and a trypsin standard. Proteolytic activity was chosen due to the ease of wrapping SWNT with amphiphilic proteins and the existence of a standardized assay. Both the colorimetric and the fluorescent assays were performed at the same pH, temperature, and substrate concentration.

A notable difference between the two assays was precision. While the colorimetric assay was sensitive to the logarithm of enzyme activity, the fluorescent assay was directly sensitive to activity. While the logarithmic sensitivity would yield a large dynamic range, this would be at the cost of precision, as errors could span orders of magnitude. Thus, this colorimetric assay is limited to order-of-magnitude applications such as purification and tracking of contamination, while the fluorescent assay could be used in more precise work, such as optimization studies.

One difficulty in using the colorimetric assay was diluting samples to fit within the dynamic range. Because the colorimetric assay tracked appearance of hydrolysis byproducts rather than disappearance of substrates, responses were susceptible to interference by species already present in sample. As a result, the dynamic range varied on a sample-by-sample basis. For example, of seven crude subtilisin samples, four returned erroneous data. This problem was compounded by a 40-minute response time. The single time-point nature of the colorimetric assay data also limited experiments to linear, enzyme-limited responses. In contrast, the fluorescent assay measured the rate of substrate disappearance and was thus tolerant of more complex samples. In 3-5 minutes, real-time data could be used to track enzyme activity in either enzyme-limited or substrate-limited regimes.

A second difficulty in using the colorimetric assay was timing of absorbance measurements. At incubation times greater than 20 minutes, color continued to develop, and sample absorbances would become indistinguishable. Because the pipetting process was not instantaneous, data was susceptible to significant error from timing of measurements. The long response time of such colorimetric assays would necessitate parallel tests which would guarantee such error.

Example 2.6. Monitoring Damage to Enzymes

Figure 5A:
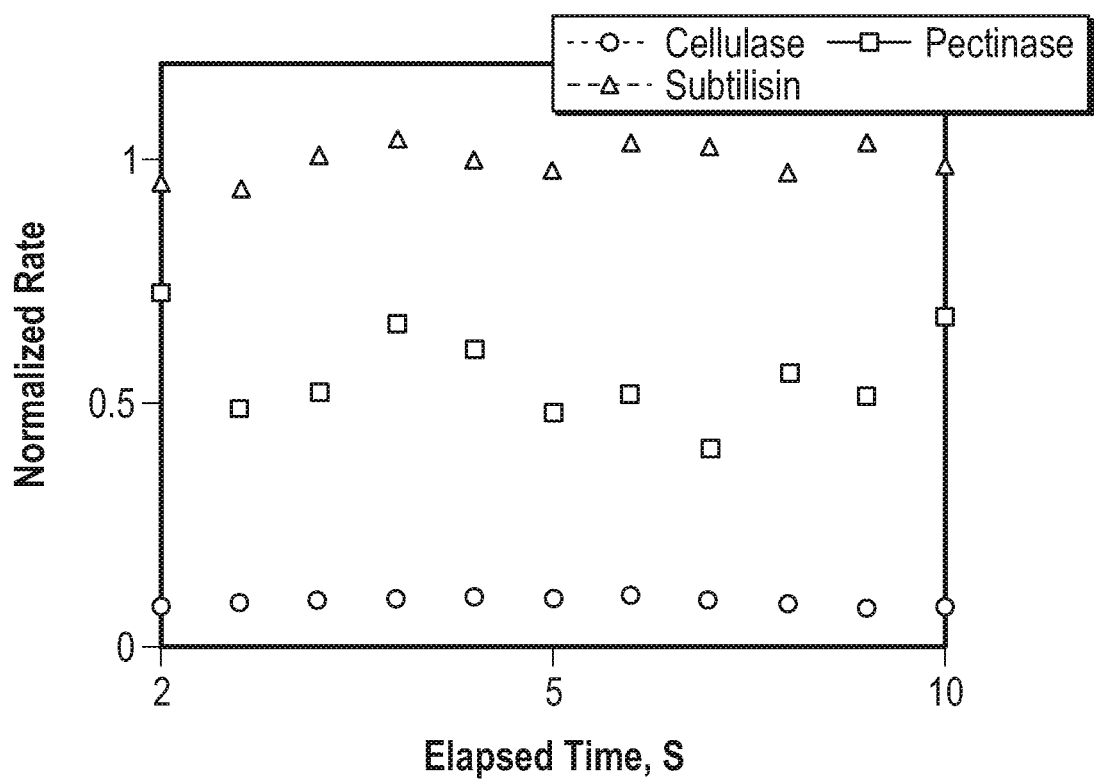
FIG. 5A shows the response profile of pectinase, cellulase, and subtilisin after repeated flash-freezing, in accordance with various embodiments.
Figure 5B:
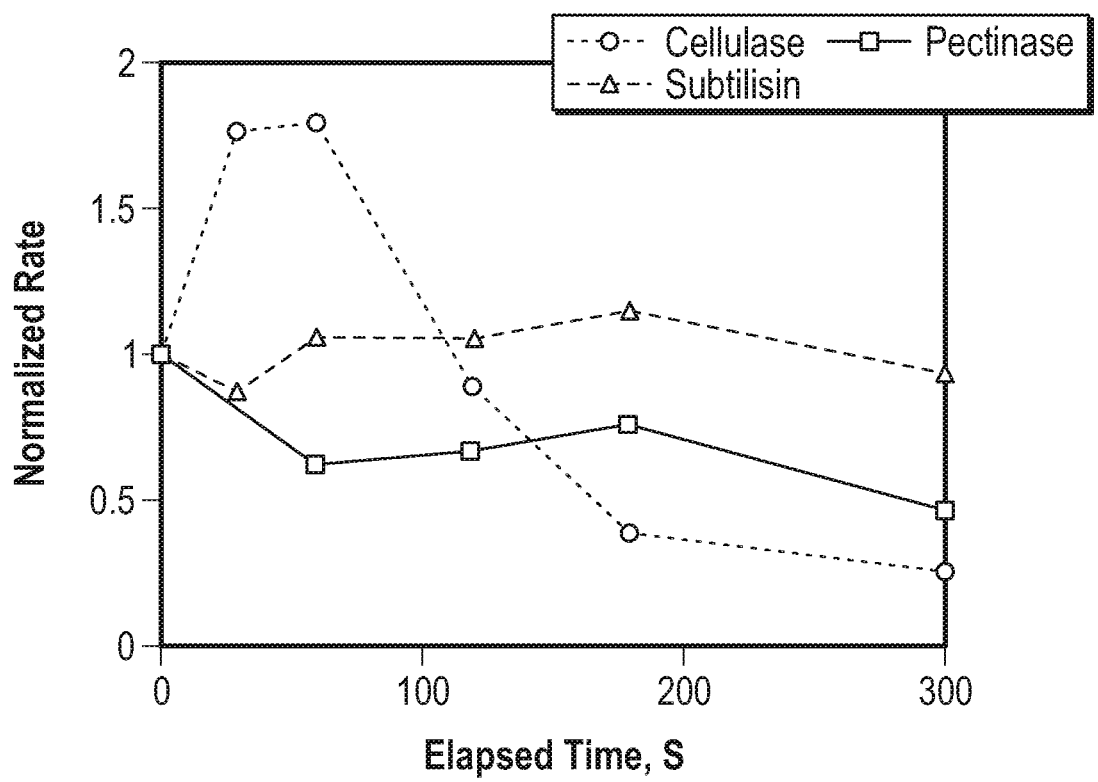
FIG. 5B shows the response profile of pectinase, cellulase, and subtilisin after repeated flash-freezing, in accordance with various embodiments.
Figure 5C:
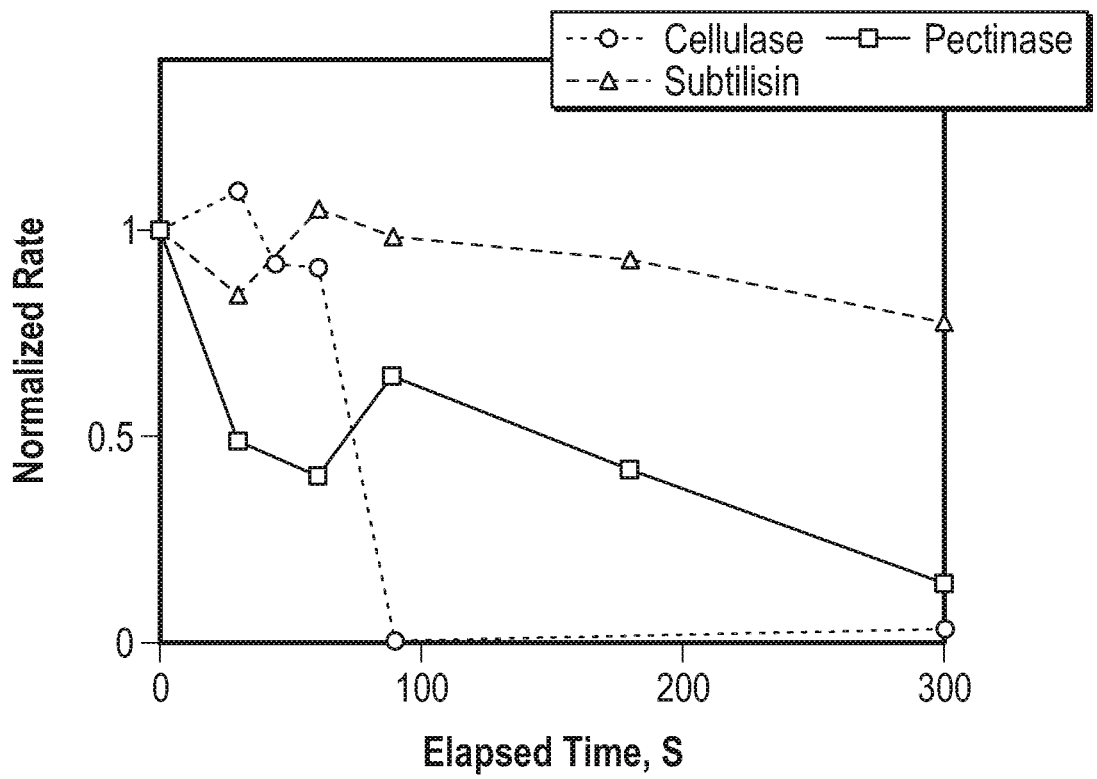
FIG. 5C shows the response profile of pectinase, cellulase, and subtilisin after repeated flash-freezing, in accordance with various embodiments.
Figure 5D:
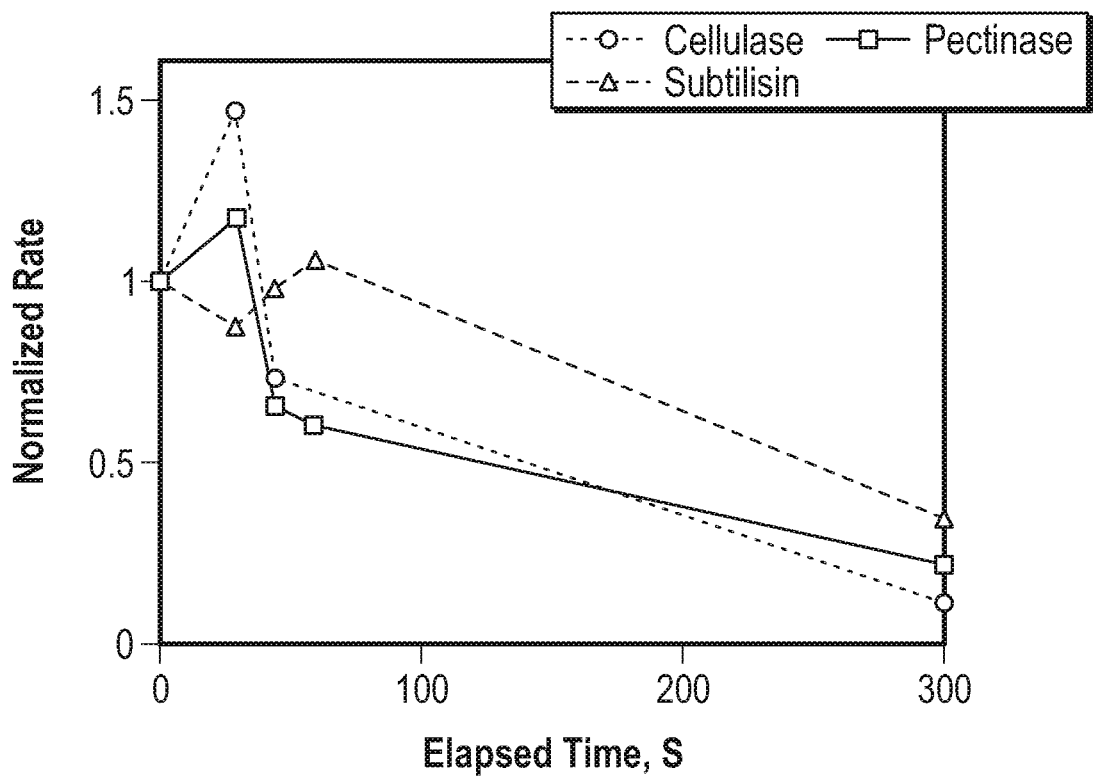
FIG. 5D shows the response profile of pectinase, cellulase, and subtilisin after repeated flash-freezing, in accordance with various embodiments.

One potential application of this assay is the monitoring of damage to hydrolytic enzymes. Damage to enzymes can occur during purification, compounding, storage (e.g., where samples are frozen and thawed), and during transportation (e.g., where samples may be exposed to elevated temperatures). To demonstrate the utility of these sensors for this application, activities of bacterial protease, pectinase, and cellulase were measured after freeze-thaw cycles and exposure to high temperatures. Response profiles were recorded after repeatedly flash-freezing enzyme samples, and predicted rate constants were compared. These profiles are shown in FIGS. 5A-5D. While measured activity was observed to fluctuate (especially for the more unstably wrapped pectin-SWNT), no significant trend was observed between the number of freeze-thaw cycles and enzyme activity (FIG. 5A). Irreversible heat damage to bacterial protease, pectinase, and cellulase was measured at temperatures of 60, 70, and 95° C. (FIGS. 5B-5D). Of the three, cellulase was found to be most sensitive to heat while bacterial protease remained functional until near-boiling conditions. High thermal stability of bacterial protease was expected when considering its widespread industrial use. Activity profiles of pectinase agreed with a prior study that calculated the half-life of this pectinase to be approximately 5 and 3 minutes at 60 and 70° C. respectively.

Example 3. Experimental Section

Example 3.1. Sensor Synthesis

To prepare wrapped nanotube solutions, 2.5 mg SWNT (Sigma, 704148) were sonicated in 5 mL substrate solution using a probe sonicator (Qsonica CL-18) for 30 minutes at 15 W. The mixture was then sonicated twice for 15 minutes at 14,000 rpm. SWNT were sonicated in 10 mg/mL pectin, casein, and CMC solutions and 2.5 mg/mL BSA and lysozyme solutions. The sensors were recovered in the supernatant. Substrate concentrations were selected based on solubility and presumed affinity to SWNT.

Example 3.2. Sensor Characterization

BSA- and lysozyme-wrapped SWNT were characterized by AFM (Agilent 5400). Subtilisin was added to these 2.5 mg/mL substrate solutions to yield a 0.5 mg/mL enzyme concentration. After incubation for approximately 20 minutes, these samples were then diluted by a factor of 10 and spotted onto mica slides. A second set of samples was scanned without addition of subtilisin.

Example 3.3. Fluorescent Assay

BSA (Carolina 842251)-wrapped SWNT were tested with Alcalase bacterial protease pellets (Carolina 202390). Citrus pectin (Sigma P9135)-wrapped SWNT were tested with Pectinex pectinase (Carolina, 202380). CMC (Sigma 419303)-wrapped SWNT were tested with a cellulase mix (Carolina 853630). Samples were tested serially in a 96-well plate with 3-5 minute scan times. Enzyme samples were added approximately 30 s into each scan to establish an initial baseline.

Example 3.4. Establishing Detection Limit

BSA-wrapped SWNT were tested with a Proteinase K (NEB P8107S) sample that was serially diluted from 20 mg/mL to 2 pg/mL at 100 times dilutions. Samples were first tested with 5-minute scans. To minimize background due to photodegradation of the substrate wrapping, single-point measurements were taken for longer tests. Samples were scanned and compared to controls at times of 1 h, 2.5 h, 24 h, and 29 h.

Example 3.5. Benchmarking Sensors with an Established Assay

A colorimetric assay was performed in a multiwell plate using the Pierce Colorimetric Protease Assay Kit (Fisher 23263). A 2.5 mg/mL casein (Carolina 853428) solution was prepared in a pH 8.5 borate buffer. Proteolysis was initiated by adding 25 μL protease solution to 100 μL of the casein solution, and the reaction was incubated for 20 min. 50 μL of 5% w/v 2,4,6-trinitrobenzene sulfonic acid were added to the solution followed by an additional 20 minutes of incubation. Absorbance at 450 nm was measured and compared to controls. This signal difference was then correlated with logarithm of enzyme concentration. A bacterial protease sample was tested compared to a trypsin standard curve with 10-times serial dilutions. Using the fluorescent SWNT probe assay (2.5 mg/mL casein solution) two activity curves were produced using 2-times serial dilutions of both proteases. Protease concentrations were selected based on the results of the Pierce colorimetric assay.

Example 3.6. Detection of Freeze-Thaw Damage

A 5-mL concentrated enzyme sample was repeatedly flash-frozen in liquid nitrogen and thawed in a 37° C. water bath. Before and after each cycle, enzyme activity was measured using the fluorescent assay. This was repeated for 10 freeze-thaw cycles.

Example 3.7. Heat Damage to Cellulase

400 μL samples of cellulase solution were aliquoted into 2-mL Eppendorf tubes and placed into a heating block (Eppendorf Thermomixer C) at selected temperatures. After incubation for a set amount of time, the tube was removed from the heat block and cooled to room temperature. The samples were then tested with the fluorescent assay. This procedure was repeated with bacterial protease and pectinase solutions.

Example 3.8. Determining Optimal Reaction Conditions

The effect of temperature and pH was determined according to a face-centered experimental design. A fixed-temperature container was made using a clear-bottom petri dish (Mattek P35GCOL-0-10-C) with a brass compression sleeve fixed at the center (Supplement 7.1). CMC-SWNT solutions were diluted from 10 mg/mL to 2 mg/mL solutions with phosphate-citric acid buffers. Buffer solutions were preheated in a constant temperature bath, and temperature was maintained by filling the outer portion of the vessel with water from the bath.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

Example 4. Phospholipase C Study

A study was conducted to test for the presence of phospholipase C (Sigma P7633). In this study, 4 ml of a solution including (6,5)-chiral SWNT at a concentration of 0.5 mg/ml were ultrasonicated alone with phosphatidylcholine at a concentration of 2.5 mg/ml to form a phosphatidylcholine wrapped SWNT.

Figure 6:
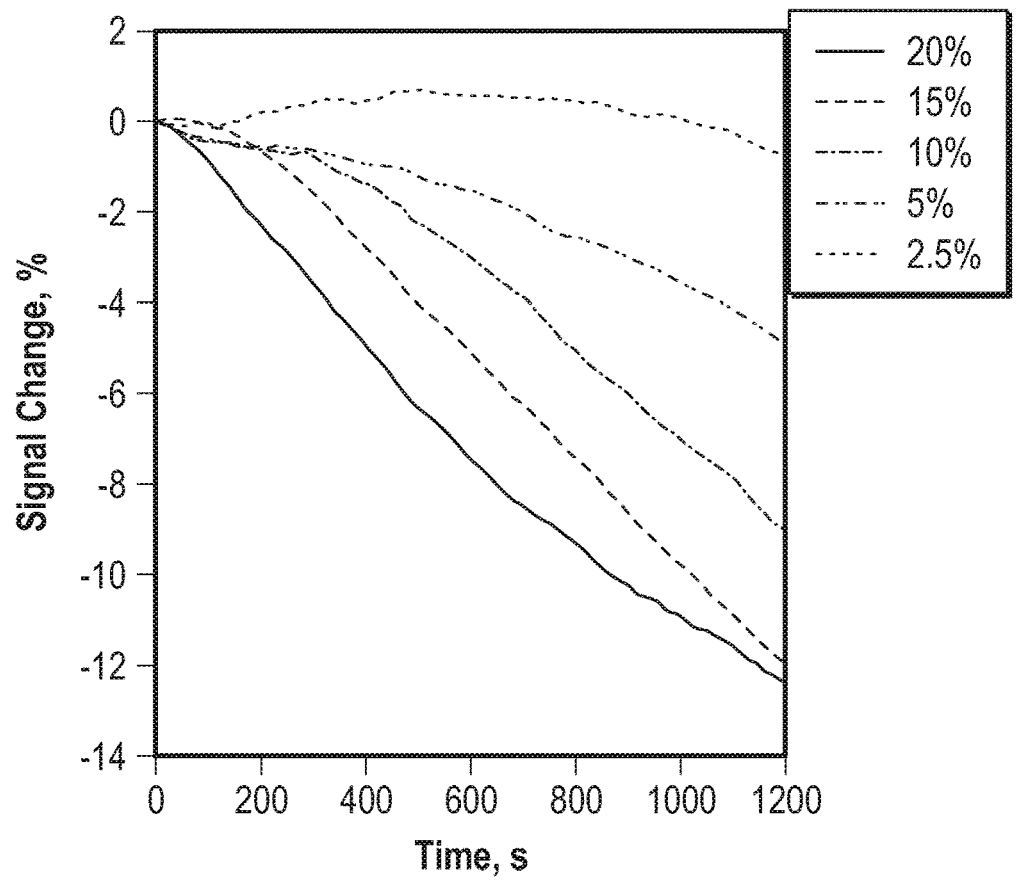
FIG. 6 shows the response of phosphatidylcholine-functionalized SWNT to different dilutions of 100 mg/mL phospholipase C solution, in accordance with various embodiments.

The phosphatidylcholine wrapped SWNT was diluted to concentrations of 2.5%, 5%, 10%, 15%, and 20% with deionized water and 20 μL of phospholipase C was added. The fluorescence signal from the solution was then measured with respect to time. FIG. 6 shows the response of phosphatidylcholine-functionalized SWNT to different dilutions of 100 mg/mL phospholipase C solution.

Example 5. Phytase Study

A study was conducted to test for the presence of Phytase. In this study, phytic acid was neutralized by incremental addition of 2M sodium hydroxide solution, 1.5 mg (6,5)-chiral SWNT were added to 3 mL of the neutralized phytate and ultrasonicated. Following centrifugation for 10 min at 14000 times gravity (×g), the supernatant was collected as a sensor solution.

Figure 7:
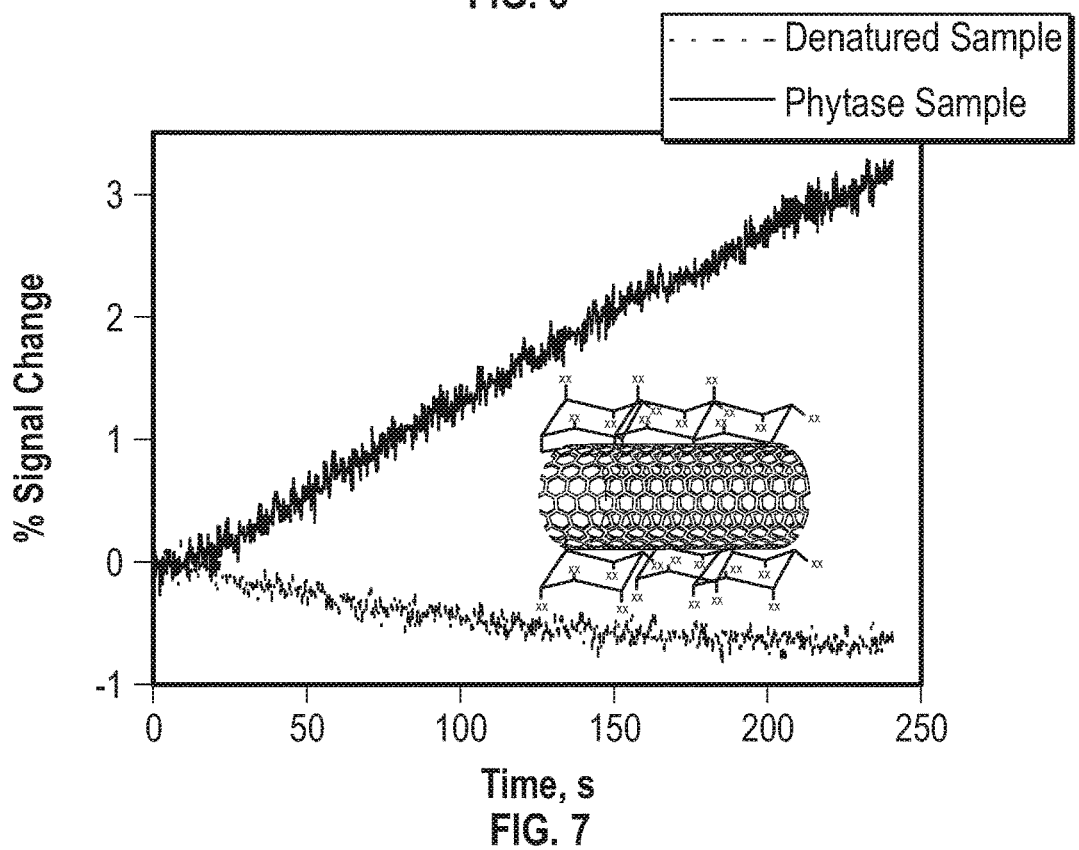
FIG. 7 shows the response over time as phytase is added and mixed with phytic acid coated SWNTs, in accordance with various embodiments.

To test responsivity to phytase, 20 μL of 10 mg/mL phytase solution were added to 100 μL sensor solution, and fluorescent signal was measured with respect to time. A control was prepared by heating a solution aliquot to 95° C. for 20 min. FIG. 7 shows the fluorescence response over time as phytase is added.

Example 6. Detecting Select Enzymes in Soil

A study was conducted to detect the presence of select enzymes in soil samples. Detection of select enzymes in soil can be useful for understanding and analyzing the soil across a farm plot. Data obtained can be useful to determine which plots or sections of plats are best suited for planting certain crops or for determining the appropriate rotation for each plot.

Figure 8A:
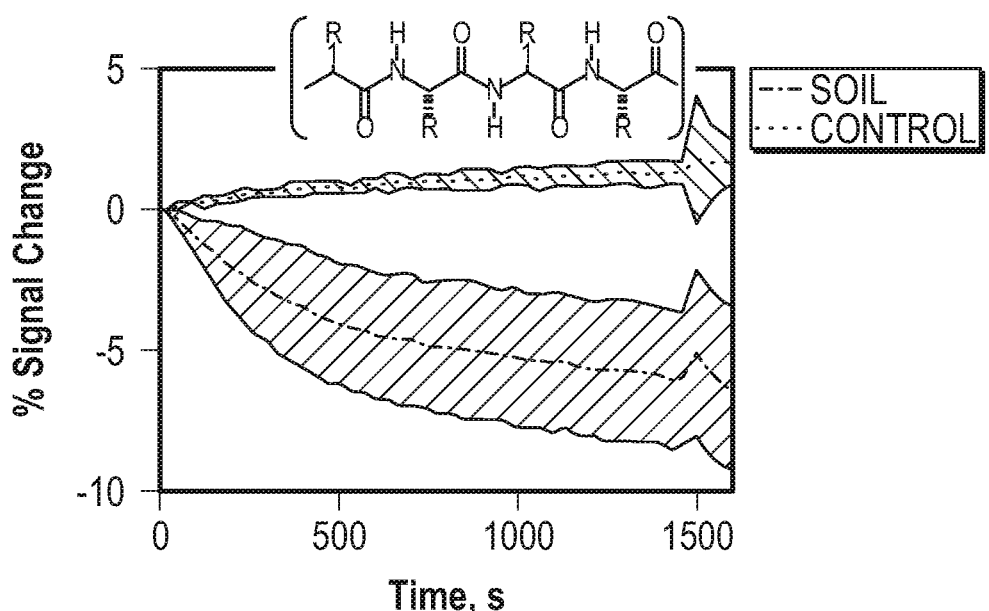
FIG. 8A is a graph showing the activity of protease when mixed with albumin coated SWNT, in accordance with various embodiments.
Figure 8B:
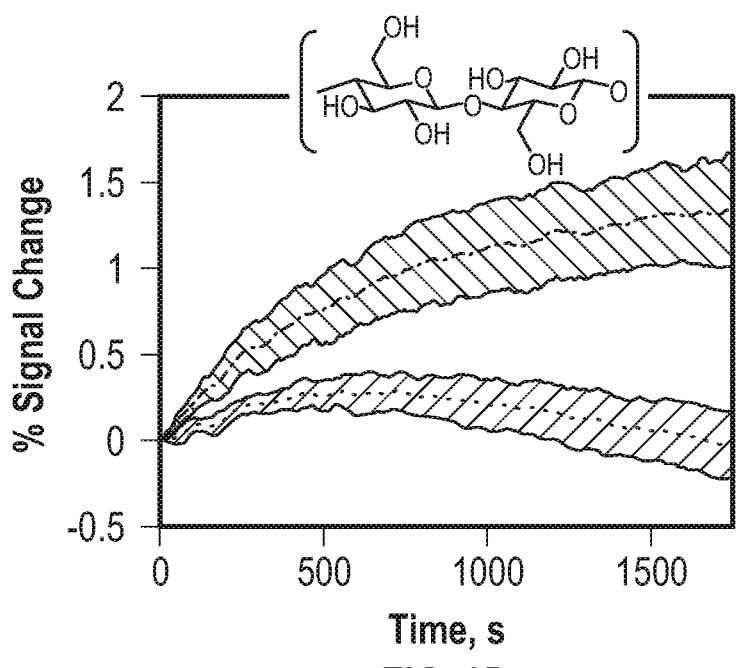
FIG. 8B is a graph showing the activity of 3-glucanase when mixed with carboxymethyl cellulose (CMC) coated SWNT, in accordance with various embodiments.
Figure 8C:
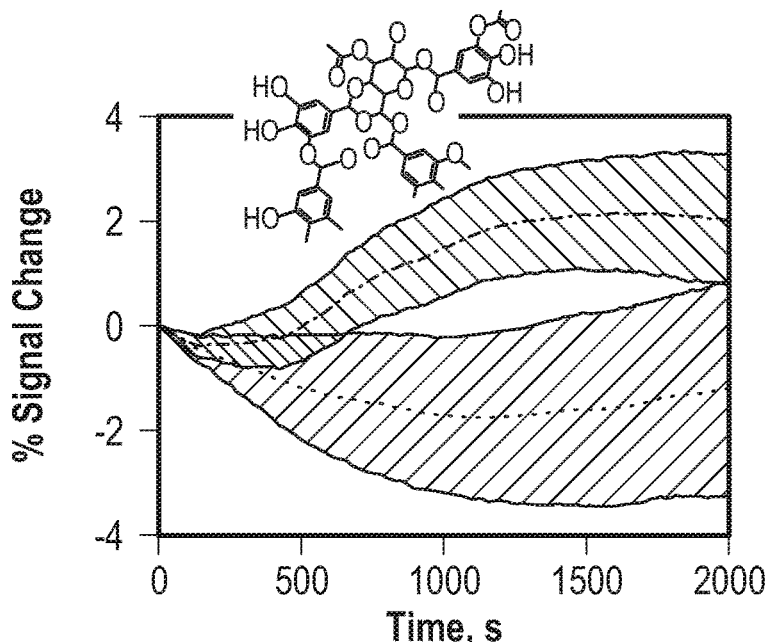
FIG. 8C is a graph showing the activity of a lignin-modifying enzyme mixed with a lignosulfonic acid coated SWNT, in accordance with various embodiments.

SWNTs were prepared with 4 ml of a solution including (6,5)-chiral SWNT at a concentration of 0.5 mg/ml were ultrasonicated alone with a substrate material of albumin (a substrate of a protease), lignosulfonic acid (a substrate of a lignin-modifying enzyme), or CMC (a substrate of a β-glucanase) at a concentration of 2.5 mg/ml to form a substrate wrapped SWNT. 1 g soil with 1 mL deionized water were combined and gently agitating. The turbid mixture was then centrifuged at 14000×g, and the supernatant was collected as a soil enzyme sample. Controls were prepared with samples that were heated in a 120° C. drying oven for 1.5 h. Fluorescence assays were performed by adding 20 μL of the respective enzyme solution to 80 μL sensor solution. FIGS. 8A-8C show the activity of the protease, β-glucanase, and lignin-modifying enzyme, respectively.

This study could be carried out by subdividing a plot into various sections to study the relative presence or absence of the enzymes described herein. The data can be obtained in a high-throughput manner using, for example, a device in which a motorized microscope stage is placed above a fluorimeter. The motorized microscope stage can include any suitable number of sample wells. Each sample well can include soil from a designated section of the plot. The motorized microscope stage can be actuated to selectively place the well in communication with the fluorimeter, which outputs an analog voltage signal to an analog-to-digital converter. Communication with the fluorimeter and motorized stage can be achieved by USB connection to a PC. Data points can be collected by integrating raw signal from individual wells and pairing with a timestamp.

Beyond testing samples from an active plot, these methods can also be used to study soil that is purchased for example from a commercial vendor or otherwise obtained. This can allow for the soil to be tested for the presence of any desirable or undesirable enzymes before it is used.

Example 7. Detecting Hyaluronidase

A study was conducted to test for the presence of hyaluronidase (Sigma H3506). In this study, 4 ml of a solution including (6.5)-chiral SWNT at a concentration of 0.5 mg/ml were ultrasonicated alone with hyaluronan at a concentration of 2.5 mg/ml to form a hyaluronan wrapped SWNT.

Figure 9:
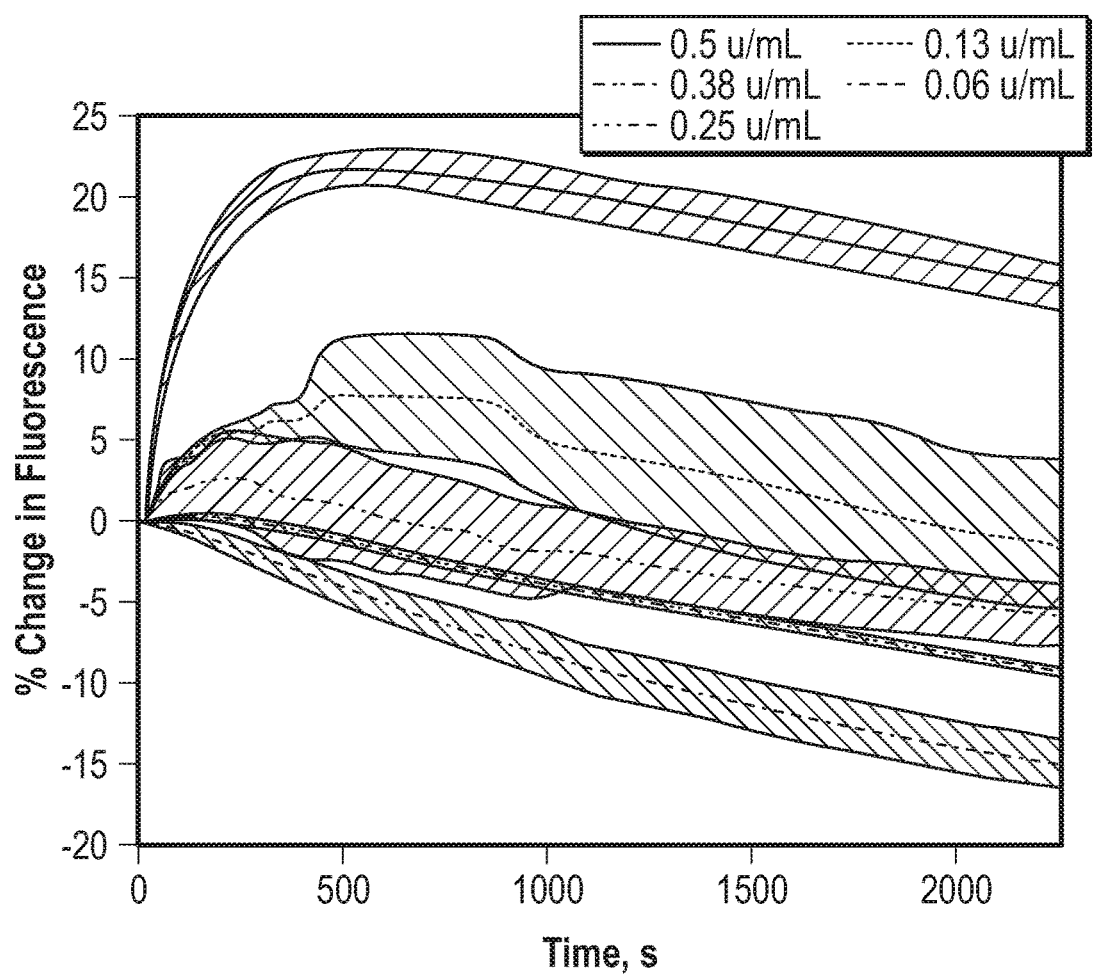
FIG. 9 shows the response of hyaluronan-wrapped SWNT to different concentrations of hyaluronidase, in accordance with various embodiments.

The hyaluronan-wrapped SWNT was diluted to concentrations of 0.06 µg/ml, 0.13 µg/ml, 0.25 µg/ml, 0.38 µg/ml, and 0.5 µg/ml with deionized water and 20 µL of hyaluronidase was added. The fluorescence signal from the solution was then measured with respect to time. FIG. 9 shows the response of hyaluronan wrapped SWNT to different dilutions of 100 mg/mL hyaluronidase solution.

The hyaluronan-wrapped SWNT was further exposed to a supernatant collected from a pancreatic cancer culture. Specifically, 10 µL of the supernatant was added to 90 µL of hyaluronan wrapped SWNT. A decrease in fluorescence was observed. Detecting hyaluronidase can be beneficial because it is overexpressed in cancers and thus detection can be used, in part, to determine the severity of an invading tumor. Identifying hyaluronidase can also help in basic, fundamental studies of tissue reconfiguration upon tumor invasion. Additionally, there are some drug formulations that use hyaluronidase as a co-molecule to help break apart the tissue around the tumor and allow for drug penetration, therefore determining whether hyaluronidase is present, can be used in drug administration decisions.

A study was conducted to detect the presence of select enzymes in soil samples. Detection of select enzymes in soil can be useful for understanding and analyzing the soil across a farm plot. Data obtained can be useful to determine which plots or sections of plats are best suited for planting certain crops or for determining the appropriate rotation for each plot.

Additional Embodiments

The following exemplary embodiments are provided, the numbering of which is not to be construed as designating levels of importance:

Embodiment 1 provides a sensor assembly probe for determining enzymatic activity comprising:
an aqueous medium comprising one or more fluorescent hydrophobic semi-conductive nanoparticles; and
an amphiphilic polymer comprising a substrate for a predetermined enzyme, the amphiphilic polymer coating at least a portion of a surface of the fluorescent hydrophobic semi-conductive nanoparticle.

Embodiment 2 provides the sensor assembly probe of Embodiment 1, wherein a morphology of the fluorescent hydrophobic semi-conductive nanoparticle comprises a nanosphere, a nanorod, a nanofiber, a nanotube, a nanostar, a nanocup, or combinations thereof.

Embodiment 3 provides the sensor assembly probe of any one of Embodiments 1 or 2, wherein at least one of a length, width, and diameter of the fluorescent hydrophobic semi-conductive nanoparticle is in a range of from about 1 nm to about 100 nm.

Embodiment 4 provides the sensor assembly probe of any one of Embodiments 1 or 3, wherein a particle size of the fluorescent hydrophobic semi-conductive nanoparticle is in a range of from about 10 nm to about 50 nm.

Embodiment 5 provides the sensor assembly probe of any one of Embodiments 1-4, wherein the fluorescent hydrophobic semi-conductive nanoparticle comprises a ceramic, a polymer, a metal carbide, a nitride, a metal, graphite, carbon, or a mixture thereof.

Embodiment 6 provides the sensor assembly probe of any one of Embodiments 1-5, wherein the fluorescent hydrophobic semi-conductive nanoparticle is a carbon nanotube.

Embodiment 7 provides the sensor assembly probe of any one of Embodiments 1-6, wherein the fluorescent hydrophobic semi-conductive nanoparticle fluoresces at frequency ranging from about 800 nm to about 1500 nm.

Embodiment 8 provides the sensor assembly probe of any one of Embodiments 1-7, wherein the fluorescent hydrophobic semi-conductive nanoparticle fluoresces at frequency ranging from about 950 nm to about 1100 nm Embodiment 9 provides the sensor assembly probe of any one of Embodiments 1-8, wherein the amphiphilic polymer is a protein, a peptide, or a mixture thereof.

Embodiment 10 provides the sensor assembly probe of any one of Embodiments 1-9, wherein the amphiphilic polymer is bovine serum albumin, citrus pectin, carboxymethyl cellulose, or a mixture thereof.

Embodiment 11 provides the sensor assembly probe of any one of Embodiments 1-10, wherein the amphiphilic polymer comprises a bond that is hydrolyzable by the predetermined enzyme.

Embodiment 12 provides the sensor assembly probe of any one of Embodiments 1-11, wherein the amphiphilic polymer comprises a bond that is an ester bond, a glycosylic bond, an ether bond, a peptide bond, an acid anhydride bond, a halide bond, a phosphorous-sulfur bond, a sulfur-sulfur bond, a carbon-phosphorous bond, a carbon-sulfur bond, or a combination thereof.

Embodiment 13 provides the sensor assembly probe of any one of Embodiments 1-12, wherein the amphiphilic polymer coats about 20% to about 100% of surface area of the fluorescent hydrophobic semi-conductive nanoparticle.

Embodiment 14 provides the sensor assembly probe of any one of Embodiments 1-13, wherein the amphiphilic polymer coats about 90% to about 100% of surface area of the fluorescent hydrophobic semi-conductive nanoparticle.

Embodiment 15 provides the sensor assembly probe of any one of Embodiments 1-14, wherein the amphiphilic polymer is the substrate for the predetermined enzyme.

Embodiment 16 provides the sensor assembly probe of any one of Embodiments 1-15, wherein the amphiphilic polymer comprises a grafted functional group that is the substrate for the predetermined enzyme.

Embodiment 17 provides the sensor assembly probe of any one of Embodiments 1-16, wherein the predetermined enzyme is a hydrolase.

Embodiment 18 provides the sensor assembly probe of Embodiment 17, wherein the hydrolase is chosen from an esterase, nuclease, phosphodiesterase, lipase, phosphatase. DNA glycosylase, glycoside hydrolase, proteases, peptidase, acid anhydride hydrolase, helicase, GTPase, and mixtures thereof.

Embodiment 19 provides the sensor assembly probe of any one of Embodiments 1-18, wherein the fluorescent hydrophobic semi-conductive nanoparticle is a first fluorescent hydrophobic semi-conductive nanoparticle and the assembly further comprises a second fluorescent hydrophobic semi-conductive nanoparticle.

Embodiment 20 provides the sensor assembly probe of Embodiment 19, wherein the first fluorescent hydrophobic semi-conductive nanoparticle and the second fluorescent hydrophobic semi-conductive nanoparticle have substantially the same composition.

Embodiment 21 provides the sensor assembly probe of Embodiment 19, wherein the first fluorescent hydrophobic semi-conductive nanoparticle and the second fluorescent hydrophobic semi-conductive nanoparticle have different compositions.

Embodiment 22 provides the sensor assembly probe of any one of Embodiments 19-21, wherein the first fluorescent hydrophobic semi-conductive nanoparticle and the second fluorescent hydrophobic semi-conductive nanoparticle fluoresce at different frequencies.

Embodiment 23 provides the sensor assembly probe of Embodiment 22, wherein the respective fluorescent signals emitted by the first fluorescent hydrophobic semi-conductive nanoparticle and the second fluorescent hydrophobic semi-conductive nanoparticle have frequencies of fluorescence that differ by about 0% nm to about 100%.

Embodiment 24 provides the sensor assembly probe of any one of Embodiments 22 or 23, wherein the respective fluorescent signals emitted by the first fluorescent hydrophobic semi-conductive nanoparticle and the second fluorescent hydrophobic semi-conductive nanoparticle have frequencies of fluorescence that differ by about 0% to about 20%.

Embodiment 25 provides the sensor assembly probe of any one of Embodiments 19-24, wherein the first fluorescent hydrophobic semi-conductive nanoparticle and the second fluorescent hydrophobic semi-conductive nanoparticle are homogenously dispersed in the aqueous medium.

Embodiment 26 provides the sensor assembly probe of any one of Embodiments 19-25, wherein the first fluorescent hydrophobic semi-conductive nanoparticle and the second fluorescent hydrophobic semi-conductive nanoparticle are heterogeneously distributed in the aqueous medium.

Embodiment 27 provides the sensor assembly probe of any one of Embodiments 1-26, wherein the amphiphilic polymer is a first amphiphilic polymer and the assembly further comprises a second amphiphilic polymer.

Embodiment 28 provides the sensor assembly probe of Embodiment 27, wherein the first amphiphilic polymer and the second amphiphilic polymer comprise a different polymer.

Embodiment 29 provides the sensor assembly probe of Embodiment 28, wherein the first amphiphilic polymer and the second amphiphilic polymer are substrates of different enzymes.

Embodiment 30 provides the sensor assembly probe of any one of Embodiments 27-29, wherein the first amphiphilic polymer coats a first portion of the fluorescent hydrophilic semi-conductive nanoparticle and the second amphiphilic polymer coats a second portion of the fluorescent hydrophilic semi-conductive nanoparticle.

Embodiment 31 provides the sensor assembly probe of any one of Embodiments 19-30, wherein the first amphiphilic polymer at least partially coats the first fluorescent hydrophobic semi-conductive nanoparticle and the second amphiphilic polymer at least partially coats the second fluorescent hydrophobic semi-conductive nanoparticle.

Embodiment 32 provides a sensor assembly comprising the probe of Embodiment 1, the sensor assembly further comprising the predetermined enzyme.

Embodiment 33 provides the sensor assembly of Embodiment 32, wherein the predetermined enzyme is a first enzyme and the assembly further comprises a second enzyme.

Embodiment 34 provides the sensor assembly probe of any one of Embodiments 1-33 or the sensor assembly of any one of Embodiments 32 or 34, wherein
the hydrophobic semi-conductive nanoparticle comprises a carbon nanotube;
the hydrophobic amphiphilic polymer comprises a protein having a hydrolyzable bond; and
the predetermined enzyme is a hydrolase.

Embodiment 35 provides a method of using the sensor assembly probe of any one of Embodiments 1-31 or the sensor assembly of any one of Embodiments 32-34, the method comprising:
measuring a first fluorescent frequency emission of the probe;
contacting the probe and the predetermined enzyme; and
measuring a second fluorescent frequency emission of the probe, wherein the second fluorescent frequency emission is less than the first fluorescent frequency emission and indicates that at least a portion the substrate has reacted with the predetermined enzyme.

Embodiment 36 provides the method of Embodiment 35, wherein the second fluorescent frequency emission is zero.

Embodiment 37 provides the method of any one of Embodiments 35 or 36, wherein a mixture of enzymes comprises the predetermined enzyme.

Embodiment 38 provides the method of any one of Embodiments 35-37, further comprising determining a rate of reaction between the substrate and the predetermined enzyme.

Embodiment 39 provides the method of Embodiment 38, wherein determining a rate of reaction comprises measuring a plurality of fluorescent signals over a predetermined amount of time to quantify the amount of substrate that is consumed by the predetermined enzyme.

Embodiment 40 provides a method of making the sensor assembly probe of any one of Embodiments 1-31, or the sensor assembly of any one of Embodiments 32-34, or used according to the method of any one of Embodiments 35-39, the method comprising:
dispersing the fluorescent hydrophobic semi-conductive nanoparticle and the amphiphilic polymer in an aqueous medium; and
mixing the fluorescent hydrophobic semi-conductive nanoparticle and the amphiphilic polymer, to form the sensor assembly.

Embodiment 41 provides the method of Embodiment 40, wherein mixing comprises sonication.

Embodiment 42 provides the method of any one of Embodiments 40 or 41, wherein mixing causes the probe to precipitate out of solution.

Embodiment 43 provides the method of any one of Embodiments 40-42, further comprising contacting the probe and the predetermined enzyme.

What is claimed is:

1. A sensor assembly probe for determining enzymatic activity comprising:
an aqueous medium comprising one or more fluorescent hydrophobic semi-conductive nanoparticles; and
an amphiphilic polymer comprising a substrate for a predetermined enzyme, wherein the amphiphilic polymer coats at least a portion of a surface of the fluorescent hydrophobic semi-conductive nanoparticle.

2. The sensor assembly probe of claim 1, wherein a morphology of the fluorescent hydrophobic semi-conductive nanoparticle comprises a nanosphere, a nanorod, a nanofiber, a nanotube, a nanostar, a nanocup, or combinations thereof.

3. The sensor assembly probe of claim 1, wherein at least one of a length, width, and diameter of the fluorescent hydrophobic semi-conductive nanoparticle is in a range of from about 1 nm to about 100 nm.

4. The sensor assembly probe of claim 1, wherein the fluorescent hydrophobic semi-conductive nanoparticle comprises a ceramic, a polymer, a metal carbide, a nitride, a metal, graphite, carbon, or a mixture thereof.

5. The sensor assembly probe of claim 1, wherein the amphiphilic polymer is a protein, a peptide, or a mixture thereof.

6. The sensor assembly probe of claim 1, wherein the amphiphilic polymer comprises a bond that is hydrolyzable by the predetermined enzyme.

7. The sensor assembly probe of claim 1, wherein the predetermined enzyme is a hydrolase.

8. The sensor assembly probe of claim 7, wherein the hydrolase is chosen from an esterase, nuclease, phosphodiesterase, lipase, phosphatase, DNA glycosylase, glycoside hydrolase, proteases, peptidase, acid anhydride hydrolase, helicase, GTPase, and mixtures thereof.

9. A method of using the sensor assembly probe of claim 1, the method comprising:
measuring a first fluorescent frequency emission of the probe;
contacting the probe and the predetermined enzyme; and
measuring a second fluorescent frequency emission of the probe, wherein the second fluorescent frequency emission is less than the first fluorescent frequency emission and indicates that at least a portion the substrate has reacted with the predetermined enzyme.

10. The method of claim 9, wherein the second fluorescent frequency emission is zero.

11. The method of claim 9, wherein a mixture of enzymes comprises the predetermined enzyme.

12. The method of claim 9, further comprising determining a rate of reaction between the substrate and the predetermined enzyme.

13. The method of claim 9, wherein determining a rate of reaction comprises measuring a plurality of fluorescent signals over a predetermined amount of time to quantify the amount of substrate that is consumed by the predetermined enzyme.

14. The method of claim 9, wherein the fluorescent hydrophobic semi-conductive nanoparticle comprises a ceramic, a polymer, a metal carbide, a nitride, a metal, graphite, carbon, or a mixture thereof.

15. The method of claim 9, wherein the amphiphilic polymer is a protein, a peptide, or a mixture thereof.

16. The method of claim 9, wherein the amphiphilic polymer comprises a bond that is hydrolyzable by the predetermined enzyme.

17. A method of making the sensor assembly probe of any one of claim 1, the method comprising:
dispersing the fluorescent hydrophobic semi-conductive nanoparticle and the amphiphilic polymer in an aqueous medium; and
mixing the fluorescent hydrophobic semi-conductive nanoparticle and the amphiphilic polymer, to form the sensor assembly.

18. The method of claim 17, wherein mixing comprises sonication.

19. The method of claim 17, wherein mixing causes the probe to precipitate out of solution.

20. The method of claim 17, further comprising contacting the probe and the predetermined enzyme.

* * * * *

UNITED STATES PATENT AND TRADEMARK OFFICE
CERTIFICATE OF CORRECTION

PATENT NO. : 10,837,045 B2
APPLICATION NO. : 16/259380
DATED : November 17, 2020
INVENTOR(S) : Reuel et al.

It is certified that error appears in the above-identified patent and that said Letters Patent is hereby corrected as shown below:

In the Specification

In Column 3, Line 49, delete "3-glucanase" and insert --β-glucanase-- therefor

In Column 4, Line 13, delete "Y.""" and insert --Y,"-- therefor

In Column 4, Line 15, delete "Y." and insert --Y,-- therefor

In Column 4, Line 15, delete "Z.""" and insert --Z,"-- therefor

In Column 4, Line 20, delete "B." and insert --B,-- therefor

In Column 5, Line 17, delete "10.000" and insert --10,000-- therefor

In Column 5, Line 21, delete "10.000" and insert --10,000-- therefor

In Column 5, Line 27, delete "2.500" and insert --2,500-- therefor

In Column 5, Line 30, delete "2.500" and insert --2,500-- therefor

In Column 6, Line 57, delete "helicase." and insert --helicase,-- therefor

In Column 8, Line 22, delete "(EC 3.6)." and insert --(EC 3.6),-- therefor

In Column 8, Lines 22-23, delete "(EC 3.9)." and insert --(EC 3.9),-- therefor

In Column 9, Line 33, delete "metabolites." and insert --metabolites,-- therefor In Column 11, Line 19, delete "conversion." and insert --conversion,-- therefor Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,837,045 B2

In Column 12, Line 21, delete "[E]T" and insert --[E]$_T$-- therefor

In Column 12, Line 56, delete "h." and insert --h,-- therefor

In Column 16, Line 16, delete "solution," and insert --solution.-- therefor

In Column 16, Line 51, delete "3-glucanase," and insert --β-glucanase,-- therefor In Column 17, Line 11, delete "(6.5)-chiral" and insert --(6,5)-chiral-- therefor In Column 18, Line 60, delete "phosphatase." and insert --phosphatase,-- therefor